United States Patent
Sakairi et al.

(10) Patent No.: US 6,838,664 B2
(45) Date of Patent: *Jan. 4, 2005

(54) MASS SPECTROMETER, MASS SPECTROMETRY, AND MONITORING SYSTEM

(75) Inventors: Minoru Sakairi, Tokorozawa (JP); Yuichiro Hashimoto, Kokubunji (JP); Masuyoshi Yamada, Ichikawa (JP); Masao Suga, Hachioji (JP); Kyoko Kojima, Hino (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/651,997

(22) Filed: Sep. 2, 2003

(65) Prior Publication Data

US 2004/0036020 A1 Feb. 26, 2004

Related U.S. Application Data

(62) Division of application No. 09/663,796, filed on Sep. 18, 2000, now Pat. No. 6,686,592.

(30) Foreign Application Priority Data

Sep. 20, 1999 (JP) .......................................... 11-266044
Aug. 10, 2000 (JP) ...................................... 2000-247937

(51) Int. Cl.[7] .......................... H01J 49/00; H01J 49/04
(52) U.S. Cl. ................................. 250/288; 250/423 R
(58) Field of Search .................................. 250/281–288, 250/324, 423 R; 73/23.41, 863.21; 315/111.21, 111.31, 506–507

(56) References Cited

U.S. PATENT DOCUMENTS

| 4,023,398 | A | 5/1977 | French et al. | |
| 5,468,452 | A | 11/1995 | Hagiwara | 422/70 |
| 5,485,016 | A | 1/1996 | Irie et al. | 250/288 |
| RE35,681 | E | 12/1997 | Mitsui et al. | 250/282 |
| 6,032,513 | A | 3/2000 | Chorush et al. | 73/23.35 |
| 6,189,461 | B1 | * 2/2001 | Miyazawa et al. | 110/345 |
| 6,483,108 | B1 | * 11/2002 | Sakairi | 250/288 |
| 6,686,592 | B1 | * 2/2004 | Sakairi et al. | 250/324 |

FOREIGN PATENT DOCUMENTS

| JP | 518996 | 7/1976 | |
| JP | 59230244 | 12/1984 | |
| JP | 3179252 | 8/1991 | |
| JP | 413962 | 1/1992 | |
| JP | 6310091 | 11/1994 | |
| JP | 8261989 | 10/1996 | |
| JP | 11-304760 | * 5/1999 | G01N/27/62 |
| JP | 11304760 | 11/1999 | |
| JP | 11304761 | 11/1999 | |
| JP | 200028579 | 1/2000 | |

* cited by examiner

*Primary Examiner*—Frank G. Font
*Assistant Examiner*—Christopher M. Kalivoda
(74) *Attorney, Agent, or Firm*—Antonelli, Terry, Stout & Kraus, LLP

(57) ABSTRACT

An ion source using a corona discharge for ionizing a sample at high efficient is provided. In the corona discharge generated at a tip end of a needle electrode by application of high voltage thereto, the direction in which the sample is introduced to the region of corona discharge and the direction in which ions are drawn out of the corona discharge region are substantially opposed to each other to improve the efficiency of ionization and to maintain a stable discharge for a long period of time.

5 Claims, 21 Drawing Sheets

(EXPLOSIVE VAPOR)

FIG. 14(a)
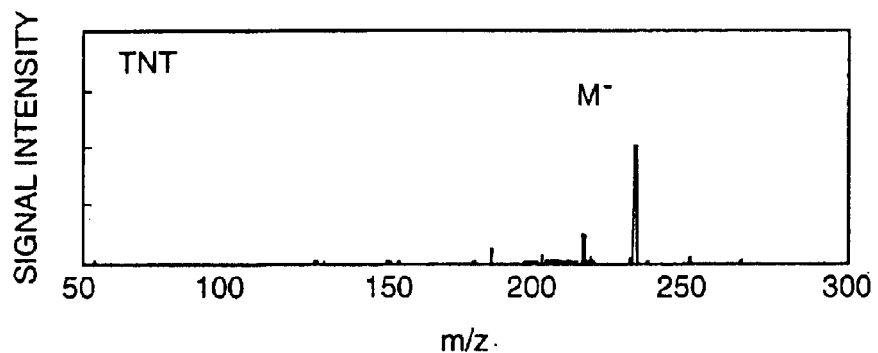
FIG. 14(b)
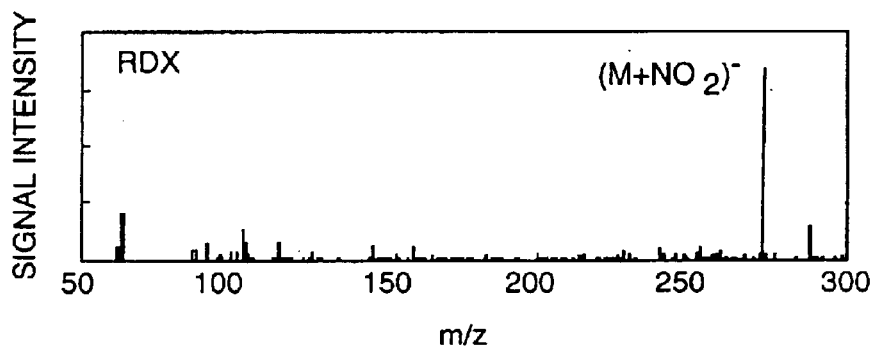
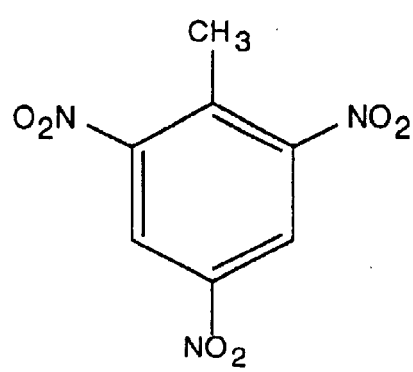
TNT
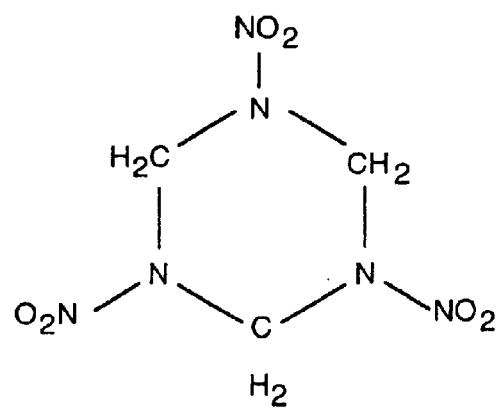
RDX
FIG. 14(c)     FIG. 14(d)

MASS SPECTROMETER, MASS SPECTROMETRY, AND MONITORING SYSTEM

CROSS-REFERENCE TO RELATED APPLICATIONS

This application is a divisional of application Ser. No. 09/663,796 filed on Sep. 18, 2000 now U.S. Pat. No. 6,686,592. The contents of application Ser. No. 09/663,796 are hereby incorporated herein by reference in their entirety.

BACKGROUND OF THE INVENTION

The present invention relates to an ion source and a mass spectrometer, and to mass spectrometry employing the ion source, as well as to a monitoring system employing the same or to a monitor employing the ion source.

Conventionally, as a method of detecting a minor component in a gas or a liquid with a high sensitivity, it has been known to detect ions generated by ionization in a measuring sample with a high sensitivity by means of a mass spectrometer.

There are various methods for ionizing a sample. One of various sample ionizing methods is an atmospheric pressure chemical ionization method employing a corona discharge. Japanese Patent Application Laid-Open No. 51-8996 (1976) discloses a method in which a sample is introduced in a corona discharge region, which is generated at the tip end of a needle electrode by applying a high voltage thereto, for ionizing the sample. At this time, in addition to the case where the sample is directly ionized by a corona discharge (primary ionization), the sample is also ionized by ion molecule reaction (secondary ionization), resulting in high efficiency ionization of the sample molecule.

On the other hand, as disclosed in Japanese Patent Application Laid-Open No. 6-310091 (1994), among ionization methods which use corona discharge, there has been proposed a method of ionizing a sample without directly introducing a sample gas into a corona discharge region. Namely, the method proposes to use primary ions generated in a separately provided corona discharge region and to efficiently perform secondary ionization of the sample molecules not passing through the corona discharge region by ion molecular reaction. This method is particularly effective for an objective sample, such as silane gas, which cannot be directly ionized using a corona discharge without extreme contamination of the ion source by the discharge product.

Furthermore, there is a method disclosed in U.S. Pat. No. 4,023,398 to French et al. In the disclosed method, a curtain of gas is blown between the corona discharge region and an aperture for introducing ions into the vacuum region in order to prevent introduction of a carrier gas into the mass spectrometric portion which is under vacuum conditions for transporting the sample. Thereby, the discharge efficiency can be improved when a vacuum discharge system, such as a cryopump, is used.

Furthermore, Japanese Patent Application Laid-Open No. 3-179252 (1991) discloses a gas flow direction. In this method, a liquid sample flows through a hollow needle electrode, and a fine droplet of the liquid sample ionized at the tip end of the needle is efficiently vaporized by a dry gas flowing in opposition thereto. On the other hand, dispersion of the ionized sample is suppressed to improve the maintenance efficiency. However, Japanese Patent Application Laid-Open No. 3-179252 (1991) does not disclose a problem in the stability of the discharge, nor a solution of such a problem.

In the method disclosed in the above-identified Japanese Patent Application Laid-Open No. 51-8996 (1976) and Japanese Patent Application Laid-Open No. 3-179252 (1991), when the concentration of the measuring sample is low (for example, upon measurement of a minor component in the air or upon measuring a minor component in a liquid), the intensity of ions of the component present in a greater amount in comparison with the ions of the measuring sample, or ions originated from a component present in a large amount (for example, an ion or the like generated by ion molecular reaction), becomes extremely high. Accordingly, when the sensitivity of a detector is adapted to the ions of the measuring sample in a fine amount, ions of the component present in a large amount or ions originated from the component present in a large amount may reach the detector to cause a large current to flow, resulting in damage to the detector, thereby to gradually degrade the amplification factor of the current.

On the other hand, when a molecule corresponding to a component present in a large amount or a molecule corresponding to ions originated from the component present in a large amount can be ionized easier than the molecule of the objective sample, the generation efficiency of the ions of the objective sample is lowered, thereby lowering the sensitivity. Furthermore, in case of an ion trap type mass spectrometer performing mass spectrometric analysis of accumulated ions by scanning a high frequency voltage after accumulating the ions, ions less than or equal to a mass number corresponding to the amplitude of the high frequency voltage to be applied may directly reach the detector after passing through an ion trap mass spectrometric portion. Accordingly, when ions are present in a large amount, the detector may be damaged, thereby to gradually degrade the amplification of the current.

On the other hand, Japanese Patent Application Laid-Open No. 3-179252 (1991) is related to an ion source for analyzing a liquid sample, but has no disclosure for analysis of gas.

Further, the method disclosed in U.S. Pat. No. 4,023,398, while providing for introduction of a carrier gas into a vacuum by using a curtain of gas, the obtained mass spectrum is nothing different from the prior art. Therefore, problems similar to those of the prior art can be expected.

Furthermore, in the prior art set forth above, the components in the gas to be measured may be deposited on the tip end of the needle, so as to make the corona discharge unstable, thereby to cause difficulty in effecting continuous measurement over a long period of time. In case of the method disclosed in Japanese Patent Application Laid-Open No. 6-210091 (1994), nothing has been discussed with respect to continuous operation over a long period, such as one month.

SUMMARY OF THE INVENTION

Accordingly, it is an object of the present invention to provide an ion source using a corona discharge for efficiently generating ions of a sample and a device employing the same.

Another object of the present invention is to provide an ion source which can maintain a stable discharge for a long period, and a device employing the same.

1) Means for Improving Ion Generation Efficiency

At first, as a means for improving ion generation efficiency, in a corona discharge generated at the tip end of a needle electrode by applying high voltage thereto, a direction connecting the needle electrode and a partitioning wall having an opening for passing the generated ions into a mass spectrometric portion, namely a direction along which the ions are drawn from the discharge region, and the direction of flow of a sample gas are different. Thereby, the efficiency of generation of ions of the objective sample can be significantly improved.

By adopting the construction as set forth above, the following effect is obtained. For example, a primary ion molecular reaction in the case where chlorophenols in dry air are monitored using a negative corona discharge becomes as follow:

$$O_2 + e^- \rightarrow O_2^-$$

(negative corona discharge)

$$O_2 + N_2 \rightarrow 2NO$$

(negative corona discharge)

$$O_2^- + NO \rightarrow NO_3^-$$

$$O_2^- + (Cp) \rightarrow (CP-H)^- + HO_2$$

Here, $(CP-H)^-$ represents a negative ion removed proton from CP. As can be appreciated from the foregoing expression, basically, $O_2^-$ generated by negative corona discharge intervenes reaction. By reaction of $N_2$ and $O_2$ under corona discharge, $NO_3^-$ is easily generated via the NO as an intermediate product. Thus, ions having a high strength can be monitored. Since $NO_3^-$ has a high acidity, it will not react with CP. Accordingly, what is monitored, when the concentration of $N_2$ is quite high in comparison with CP, is mostly $NO_3^-$, and little $(CP-H)^-$ is monitored.

Among such reaction processes, when the reaction of $O_2^- + NO \rightarrow NO_3^-$ can be restricted, the reduction of $O_2^-$ can be suppressed. By this, $O_2^- + CP \rightarrow (CP-H)^- + HO_2$ is progressed. Thus, $NO_3^-$ possibly generated in a large amount can be significantly reduced. Accordingly, the amount of the objective (CP-H) which is generated can be increased. For restricting generation of $NO_3^-$, it is important not to form overlapping regions of $O_2^-$ and NO. One approach for this is to make the direction of ion movement different from the direction of the intermediate product flow by use of an electric field, thereby to make the period during which the intermediate is present in the corona discharge region extremely short. Particularly, when the foregoing two directions are opposite, a significant effect can be achieved. At this time, in the reaction process set forth above, the presence of the intermediate product NO can be ignored. Accordingly, the foregoing reaction becomes substantially:

$$O_2 + e^- \rightarrow O_2^-$$

(negative corona discharge)

$$O_2^- + CP \rightarrow (CP-H)^- + HO_2$$

This mode of reaction is quite desirable from the point of view of monitoring $(CP-H)^-$ with a high precision.

2) Means for Maintaining the Discharge for a Long Period

The present invention provides a mass spectrometer and relates to mass spectrometry. In a mass spectrometer, having an ion source performing ionization of a sample by generating a corona discharge at the tip end of a needle electrode through application of a high voltage to said needle electrode, the ion source is constructed so that the angle between the direction, in which the ions pass from the needle electrode to the opening for introducing the generated ions into the mass spectrometric portion, namely the direction along which the ions are drawn from the discharge region, and the direction of flow of the sample gas is greater than or equal to 90°. (In other views, a line extending from the first opening for feeding ions to the mass spectrometric portion to the tip end of the needle electrode, and a line extending in the direction of sample gas flow into the discharge region form an angle which is less than or equal to 90°).

With the construction set forth above, in addition to improvement of the ion generation efficiency of the measurement objective substance, a stable discharge can be maintained for a long period. One of the reasons for this will be discussed in terms of a negative corona discharge.

The reason why a stable discharge cannot be maintained for a long period when a gas flow is not present in the discharge region is that components in the gas are deposited on the tip end of the needle electrode to make the curvature of the tip greater, causing instability in the discharge. In such a case, fluctuation is caused in the current value of the discharge to make the ionization unstable and the ion strength measured by the mass spectrometer also fluctuates. In order to perform an analysis with high reliability, maintenance to frequently change the needle electrode and sharpening the tip end of the needle electrode is required.

When a negative corona discharge is used, an electron which is discharged from the tip end of the needle electrode with a negative high pressure is caused to collide with a neutral molecule in the gas to cause ionization. The ionizing region is quite close to the tip end (within 1 mm). The negative ion generated in this way moves toward the counter electrode in response to the electrical field generated between the needle electrode and the counter electrode. The phenomenon whereby the radius of curvature at the tip end of the needle electrode becomes greater, results in fluctuation of the discharge current value for the following reasons.

1) The negative ions generated in the ionizing region in the vicinity of the tip end of the needle electrode may weaken the field intensity in the tip end region of the needle electrode.
2) When the field intensity is weakened, the discharge current drops.
3) The negative ions generated in the ionizing region move toward the counter electrode in response the force of the electric field.
4) The field intensity in the tip end region of the needle electrode becomes enhanced again.

By repetition of the foregoing steps 1) to 4), the discharge current flows. When the radius of curvature of the tip end of the needle electrode is small, even if the field intensity is weakened, the discharge current may not be lowered to permit continuous discharge. However, if the radius of curvature of the tip end of the needle electrode is increased, due to the effect of the space charge of the negative ions, the field intensity is lowered, which results in lowering of the discharge current. When the voltage is lowered in order to prevent lowering of the discharge current, the discharge mode may transit from corona discharge to spark discharge, thereby to make discharge mode unstable, which is not suited for analysis.

When the flow of gas is produced in the ionizing region, the negative ions which possibly cause a space charge are dispersed to restrict the lowering of the field intensity at the tip end of the needle electrode.

Accordingly, by generating a gas flow at the tip end region of the needle electrode, stable discharge can be maintained even when the radius of curvature of the tip end of the needle electrode becomes large due to deposition to a certain extent.

When the sample gas flows from the root side of the needle, the region for actively causing ionization in the vicinity of the tip end of the needle electrode becomes disturbed, thereby to cause difficulty in efficiently dispersing the space charge.

On the other hand, by providing a function for monitoring the discharge current value, when the amplitude of the current value becomes greater than or equal to a certain value, an alarm can be given for exchanging the needle, the whereby maintenance timing for replacement of the needle electrode can be determined properly.

BRIEF DESCRIPTION OF THE DRAWINGS

The present invention will be understood more fully from the detailed description given hereinafter and from the accompanying drawings of the preferred embodiment of the present invention, which, however, should not be taken to limit to the invention, but are provided for explanation and understanding only.

FIGS. 14(a) and 14(b) are views showing examples of a mass spectrum to be obtained from the ion source of the present invention;

FIGS. 14(c) and 14(d) are molecular diagrams for TNT and RDX, respectively;

DESCRIPTION OF THE PREFERRED EMBODIMENTS

The present invention will be discussed hereinafter in detail in terms of a preferred embodiment of the present invention with reference to the accompanying drawings. In the following description, numerous specific details are set forth in order to provide a thorough understanding of the present invention. It will be obvious, however, to those skilled in the art that the present invention may be practiced without these specific details. On the other hand, well-known structure may not be shown in detail in order to avoid unnecessary obscurity of the present invention.

Application to a Dioxin Monitor

An ion source according to the present invention will be discussed in terms of application to a dioxin monitor.

A mass spectrometer employing an ion source according to the present invention is directly connected to an incinerator or the like, and this mass spectrometer can perform continuous monitoring of components in the exhaust gas obtained from the incinerator. Particularly, it becomes possible to significantly reduce the generated amount of dioxins by measuring dioxins or chlorobenzens, chlorophenols, hydrocarbons as a precursor discharged from the incinerator and by controlling the combustion condition of the incinerator depending upon the result of measurement.

Figure 1:
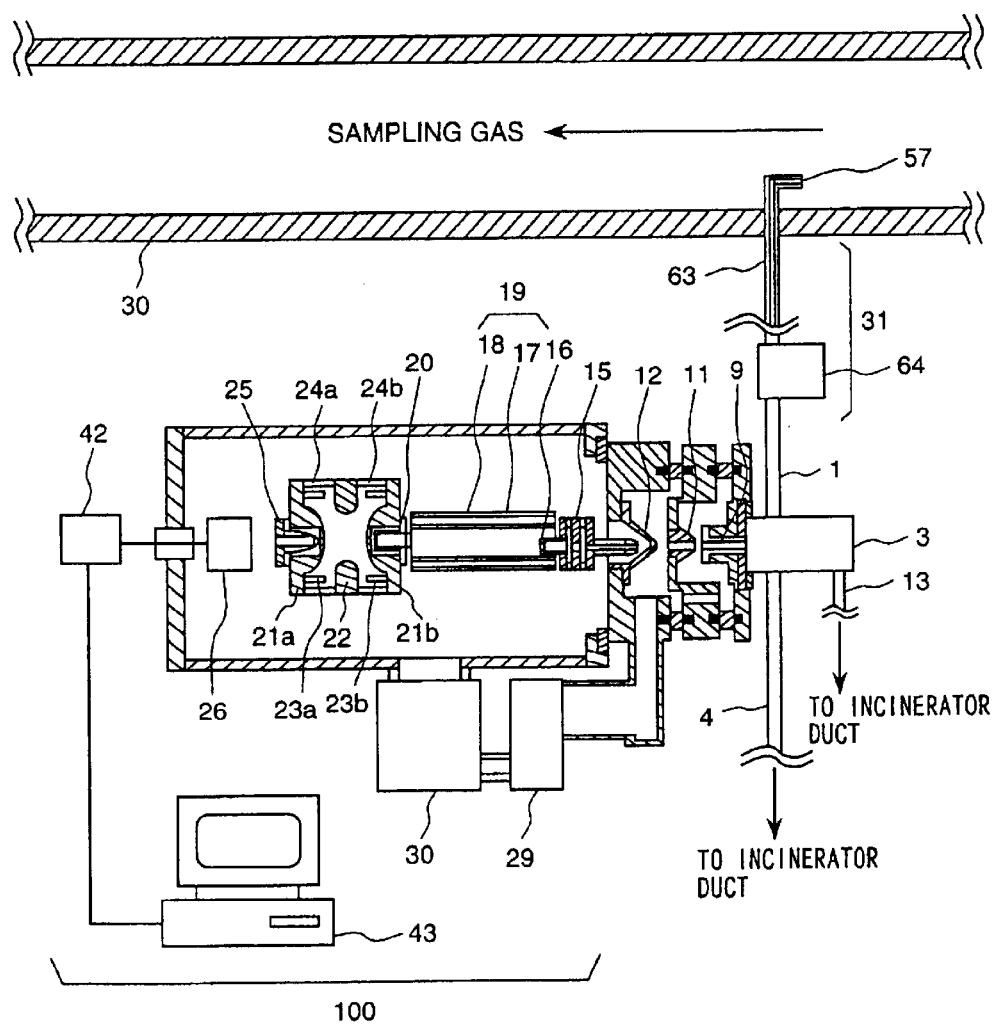
FIG. 1 is a schematic cross-sectional view showing an example of an apparatus intended to perform dioxin monitoring by means of a mass spectrometer having an ion source according to the present invention.
Figure 2:
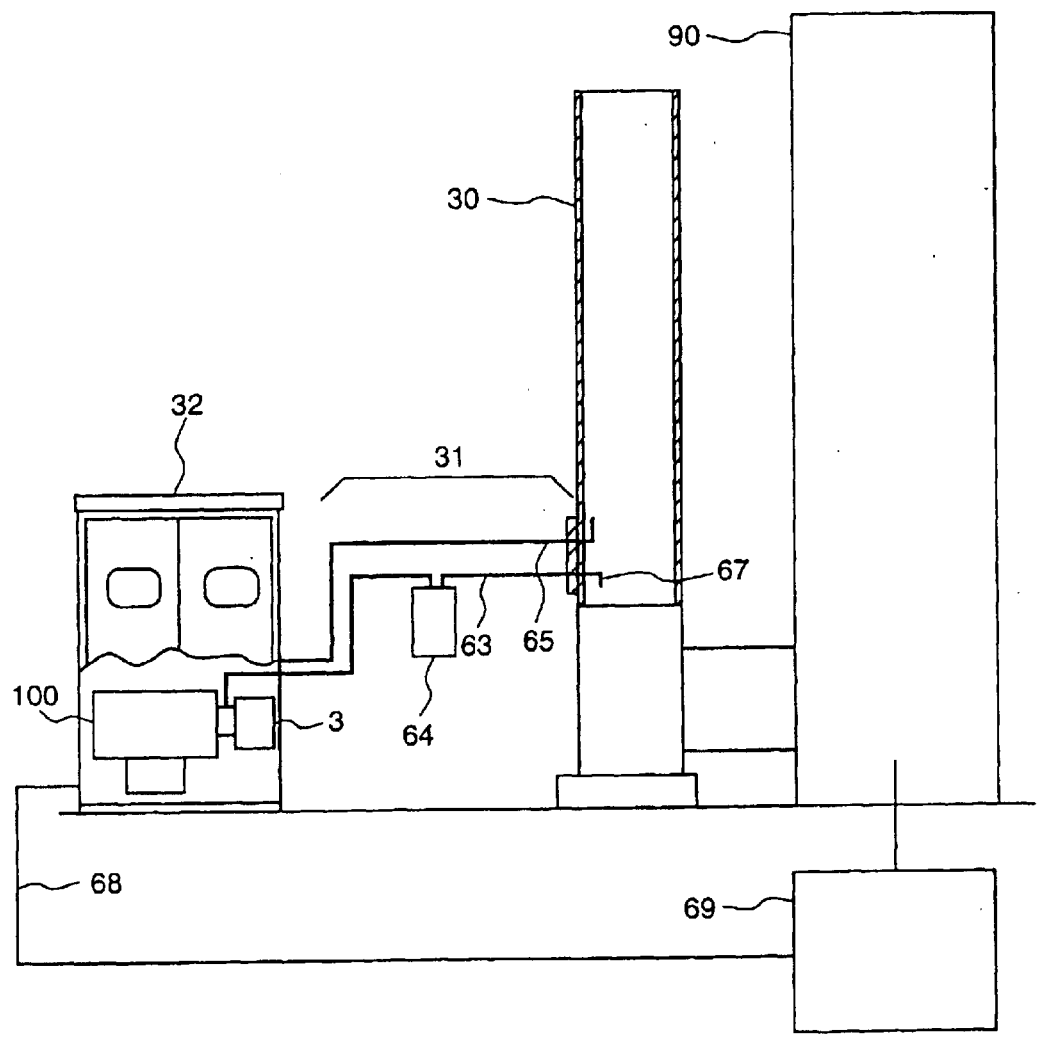
FIG. 2 is a diagram, partly in section, showing an example of a system intended to perform dioxin monitoring by means of a mass spectrometer having an ion source according to the present invention.

FIGS. 1 and 2 show an embodiment of a monitoring system according to the present invention. In this case, the monitoring system is constructed with a gas sampling part 31 for sampling a sample gas obtained from a flue gas duct 30 of the incinerator 90, a monitor 32 for detecting a measurement objective substance in the sample gas, and a combustion control device 69 for using the result of detection to control combustion, and so forth. The monitor 32 comprises a mass spectrometer employing an ion source according to the present invention.

The gas sampling part 31 is constructed with an exhaust gas inlet pipe 63 and a filter 64 for feeding the sampled gas to the monitor 32 stably, without loss due to absorption or condensation of the measurement objective substance along the way, and at a constant flow rate, and an exhaust gas outlet pipe 65 to return to the flue gas to the duct 30. For this purpose, the overall gas sampling part 31 is heated to a temperature in a range of about 100° C. to about 300° C. The filter 64 is designed for avoiding penetration of dust or the like contained in the exhaust gas of the incinerator into the monitor 32 and is provided in the vicinity of the flue gas duct 30 so as to reduce contamination at the exhaust gas inlet pipe 63, the monitor 32 and so forth, as much as possible. In the monitor 32, the measurement objective substance in the fed sample gas is selectively and efficiently ionized, and mass spectrometric analysis of the generated ions is performed in the mass spectrometer 100 for continuously detecting the measurement objective substance.

From an ion current value for a mass number originated from the measurement objective substance, a relationship can be derived between an amount of preliminarily prepared substance and an ion current value (analytical curve), presenting the amount of the objective substance. For example, in case of 2, 3-dichlorophenol (molecular weight is 162 and mass number of monitored ions is 161), the variation of the ion strength in relation to the concentration of the sample gas is measured to generate an analytical curve. On the basis of this, from the monitored ion strength, the concentration of the sample gas is estimated. The obtained data is further cleaned up before being stored together with the concentration of the component and other parameters, and in conjunction therewith, the data is output to a CRT or a printer. On the other hand, the obtained data is also fed to a combustion control unit 69 as data for controlling combustion in a garbage incineration plant via a signal line 68, for performing combustion control in the incinerator 90.

Chlorobenzens as a precursor of dioxin captures one electron to generate a molecular ion $M^-$. Chlorophenols provide a pseudo molecular ion $(M-H)^-$. In case of trichlorophenol containing three chlorine atoms, $M^-$ can be monitored. Dioxins include $(M-Cl)^-$, $(M-Cl+O)^-$ and so on in addition to molecular ion $M^-$. By selectively detecting these characteristic peaks, high sensitivity measurement with high selectivity can be performed.

For estimating the dioxin concentration from the concentration of chlorobenzens and chlorophenols, a preliminarily derived correlation is used. Since the correlation will be slightly different depending upon the system, type and so forth of the incinerator or the like, it is preferable to preliminarily obtain data of the correlation of the incinerator to which the monitor is installed in order to estimate the dioxin concentration at a higher precision.

When an ion trap mass spectrometer is used, an even higher selectivity can be obtained in comparison with the normal mass spectrometer. It uses a MS/MS method, in which energy is infused to the molecular ions captured within the ion trap mass spectrometer to cause collision with a buffer gas (He or the like) within the electrode to cause dissociation of the molecular ions. In case of an organic chlorine-based chemical compound, an ion releasing one or two chlorine atoms from the molecular ion is monitored by the MS/MS method. For example, in case of 2, 4-dichlorophonol, upon ionization using a negative corona discharge, a negative ion of $(M-H)^-$ (M: molecule, H: hydrogen) is generated. Dissociating this negative ion by the MS/MS method, a negative ion released one chlorine atom is generated. Monitoring this negative ion may provide a quite high selectivity. By determining the quantity of negative ion amount released one chlorine atom from the peak intensity, the amount of dichlorophenol in the exhaust gas can be estimated. When a plurality of kinds of molecular species to be measured are present, this measurement process may be repeated. In case of dioxins, a COCl releasing process is monitored in addition to a chlorine releasing process. Particularly, releasing of COCl is a process monitored only in dioxins. Conversely, when this process is monitored, it can be said that the presence of TCDD or toxic dioxins is proven. In case of an organic chlorine-based chemical compound, when the amount of chlorine is increased, a chemically stable substance is formed. Therefore, in case of dioxins having a large amount of chlorine, a dioxin precursor or the like, it is effective to dissociate foreign matter overlapping the measuring objective ion from the measuring objective ion, so as to measure the measuring objective ion with a high sensitivity.

In the foregoing example, discussion has been directed mainly to a case where the atmospheric pressure chemical ionization method of negative ionizing mode is used. Various components are contained in the exhaust gas. Concerning a hydrocarbon type of aromatic compound represented by benzene or the like, measurement by the atmospheric pressure chemical ionization method in a positive ionization mode becomes possible. For example, in case of benzene or monochlorobenzene, the ion species of $M^+$ is generated by the atmospheric pressure chemical ionization method in the positive ionization mode. Accordingly, in an actual sample gas measurement, by alternately measuring positive and negative ionization modes, it is possible to increase information amount in the sample gas.

Here, discussion has been given for monitoring of dioxin and compounds associated therewith in the exhaust gas mainly emitted from the incinerator. However, dioxin and its associated compounds contained in the exhaust gas discharged during a metal refining process or atmospheric air may also be monitored by a similar device and similar method. By use of the monitoring device, how much dioxins are contained in the exhaust gas of the incinerator or the like and how much fluctuation is caused can be determined directly to achieve real time dioxin monitoring. Furthermore, from initiation of combustion in the incinerator to the discharge of an exhaust in the flue to the atmosphere, the exhaust gas passes through various spaces of different temperatures and is subject to various chemical processes applied to the exhaust gas. In each of these complicated processes, generation and decomposition of dioxin and so forth can be traced. Naturally, it thus becomes possible to obtain information for modification and optimization of process conditions for reducing dioxins. Also, upon analyzing a fine component in other gases, the device and method will be effective in view of highly efficient ionization and extension of the life time.

Figure 3:
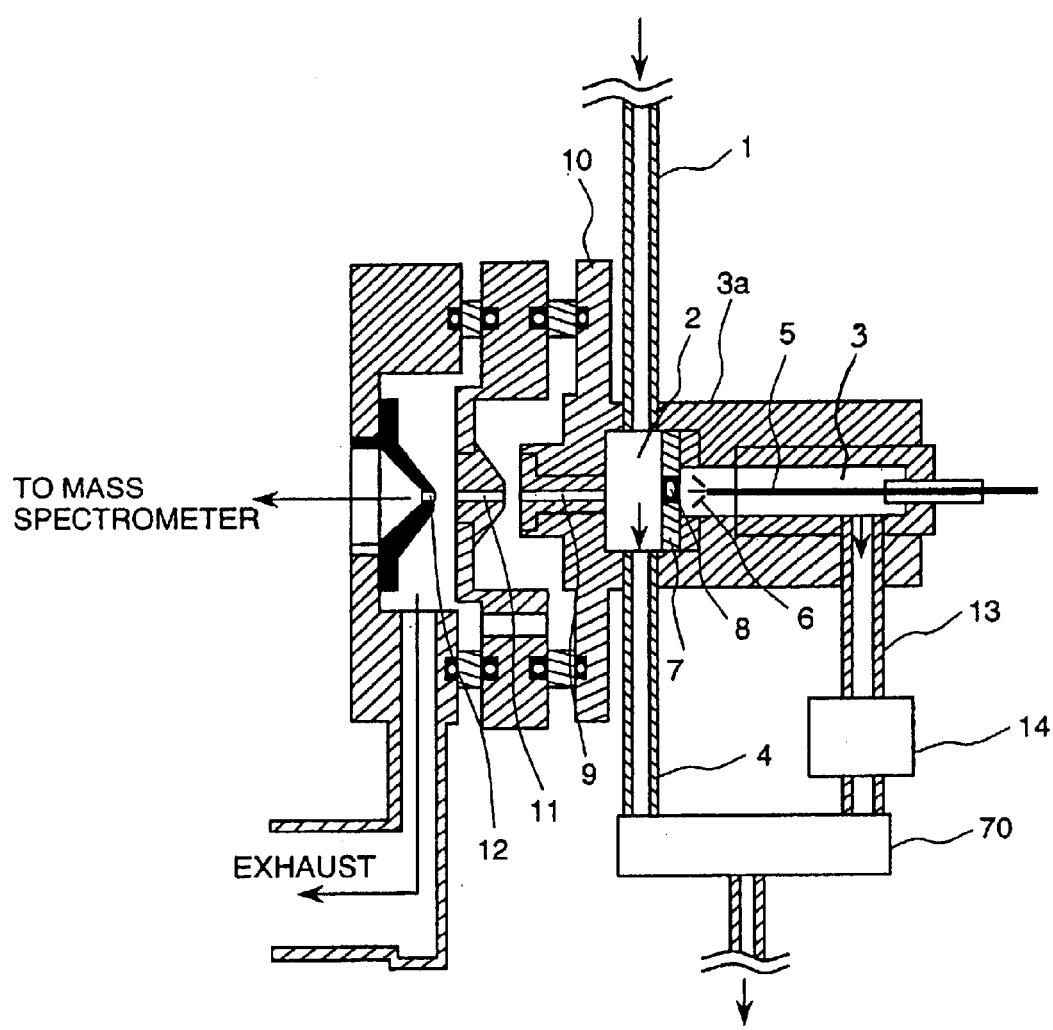
FIG. 3 is a cross-sectional view of the ion source.
Figure 4:
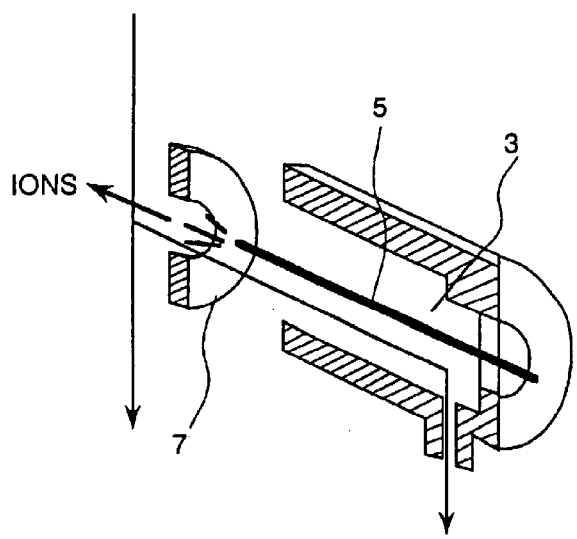
FIG. 4 is a cross-sectional diagram showing a perspective view of the ion source according to the present invention.

FIG. 3 shows a construction of the ion source characterized by substantially opposing the direction in which the sample is introduced to the corona discharge region and the direction in which ions are withdrawn from the corona discharge generated at a tip end of the needle electrode by application of a high voltage thereto, and is a partially enlarged view of FIG. 1. The arrangement of the direction in which the sample is introduced to the corona discharge region and the direction in which ions are withdrawn from the corona discharge is significantly different in comparison to the prior art. FIG. 4 is an illustration showing a part of three-dimensional construction of the ion source.

The sample introduced through a sample feed pipe 1 is first introduced into the ion drift region 2. The ion drift region 2 is placed in a substantially atmospheric pressure condition. A part of the sample introduced into the ion drift region 2 is introduced into a corona discharge region 3, and the remaining sample is discharged out of the ion source through a sample output pipe 4. The sample portion which passes into the corona discharge region 3 is introduced into a corona discharge region 6 where a corona discharge is generated at the tip end of the needle electrode 5 through application of a high voltage thereto, and the sample is ionized therein. At this time, the sample is introduced in a direction substantially opposing the flow of ions drifting toward the counter electrode 7 from the needle electrode 5. The generated ions are introduced into the ion drift region 2 from the corona discharge region 3 through an opening 8 of the counter electrode 7. At this time, by applying a voltage between the counter electrode 7 and the first ion sampling aperture 9, drifting ions will be efficiently introduced into the first ion sampling aperture 9. Ions which pass through the first ion sampling aperture 9 will be introduced into the mass spectrometer 100 under a vacuum condition through a second ion sampling aperture 11 and third ion sampling aperture 12. A region where the first ion sampling aperture 9, second ion sampling aperture 11 and third ion sampling aperture 12 are present, is a differential exhaust region for connecting the ion drift region 2, which is in a substantially atmospheric pressure condition, and the mass spectrometer, which is under a vacuum condition.

On the other hand, it is important to control the flow rate of the sample to be introduced into the corona discharge region 6 for measuring the ions stably and with a high precision. Therefore, an sample outlet pipe 13 from the ion source and a flow controller 14 of the ion source are coupled to the corona discharge region 3. On the other hand, with a view toward prevention of absorption of the sample in the ion drift region 2 and the corona discharge region 3, it is important to heat these regions. The flow rate of the sample passing through the sample outlet pipe 13 from the ion source and the flow rate of the sample passing through the flow controller 14 of ion source can be determined by the capacity of intake pump 70, such as a diaphragm pump, and the conductance of the piping provided downstream thereof. As set forth above, one of the characteristics of the ion source of the present invention is that the intake pump 70 for introducing the sample into the corona discharge region is provided on the ion outlet pipe 13 side of the ion source or the flow controller 14 side of ion source instead of in the sample feed pipe 1. Namely, absorption or the like of the sample in the suction pump 70, which can be a problem in the case where the intake pump 70 is arranged on the side of the sample feed piping 1, is avoided with this arrangement.

Hereinafter, further details of the embodiment will be discussed.

The sample introduced through the sample feed pipe 1 is first introduced into the ion drift region 2. A part of the sample which flows into the ion drift region 2 is introduced into the corona discharge region 3 (3a is a main body thereof), and the remainder of the sample is discharged out of the ion source through the sample output pipe 4. For the sample introduced through the sample feed pipe 1, the flow rate of the sample passing through the sample outlet pipe 13 from the ion source is about 10 to 2000 ml/min. It should be noted that, as the sample feed pipe 1 and the sample output pipe 4, ¼ inch stainless electrolytically polished piping or stainless piping coated with fused quartz on the inner peripheral surface may be used. The part of the sample which passes into the corona discharge region 3 is introduced into the corona discharge region 6 where a corona discharge is generated at the tip end of the needle electrode 5 by application of high voltage thereto for effecting ionization of the sample. When positive ions are to be generated, about 1 to 6 kV is applied to the needle electrode 5, and when negative ions are to be generated, about −1 to −6 kV is applied to the needle electrode 5. At this time, it is important to cause a discharge between the tip end of the needle electrode 5 and the counter electrode 7 instead of between the tip end of the needle electrode 5 and an outer wall of the corona discharge region 3a located therearound. An electric field is formed for shifting the ions generated at the tip end of the needle electrode 5 in the direction of the counter electrode 7. Accordingly, the distance between the tip end of the needle electrode 5 and the counter electrode 7 (about 3 mm) is shorter than the distance between the tip end of the needle electrode 5 and the outer wall 3a of the corona discharge region 3 located therearound (about 5 mm). At this time, the sample is introduced in a direction substantially transverse to the flow of the ions which are drifting toward the counter electrode 7 (distance between the needle electrode 5 and the counter electrode 7 is about 3 mm) from the needle electrode 5. The ions generated in the corona discharge region at the tip end of the needle electrode 5 pass into the ion drift region 2 through the opening 8 (about 2 mm of diameter) in the counter electrode 7 (about 30 mm of diameter, 2 mm of thickness). At this time, by applying a voltage between the counter electrode 7 and the first ion sampling aperture 9, ions will be caused to drift by the electric field to efficiently introduce them into the first ion sampling aperture 9. In this case, a direction extending from the tip end of the needle electrode 5 through the center of the opening portion 8 through which the generated ions are introduced into the mass spectrometer and a direction to in which the sample flows through the opening portion 8 are coextensive but opposite (opposing flows). On the other hand, the opening (sample outlet pipe 13) from which the sample gas is discharged, is located at a position inclined toward the tip end of the needle electrode.

Figure 7:
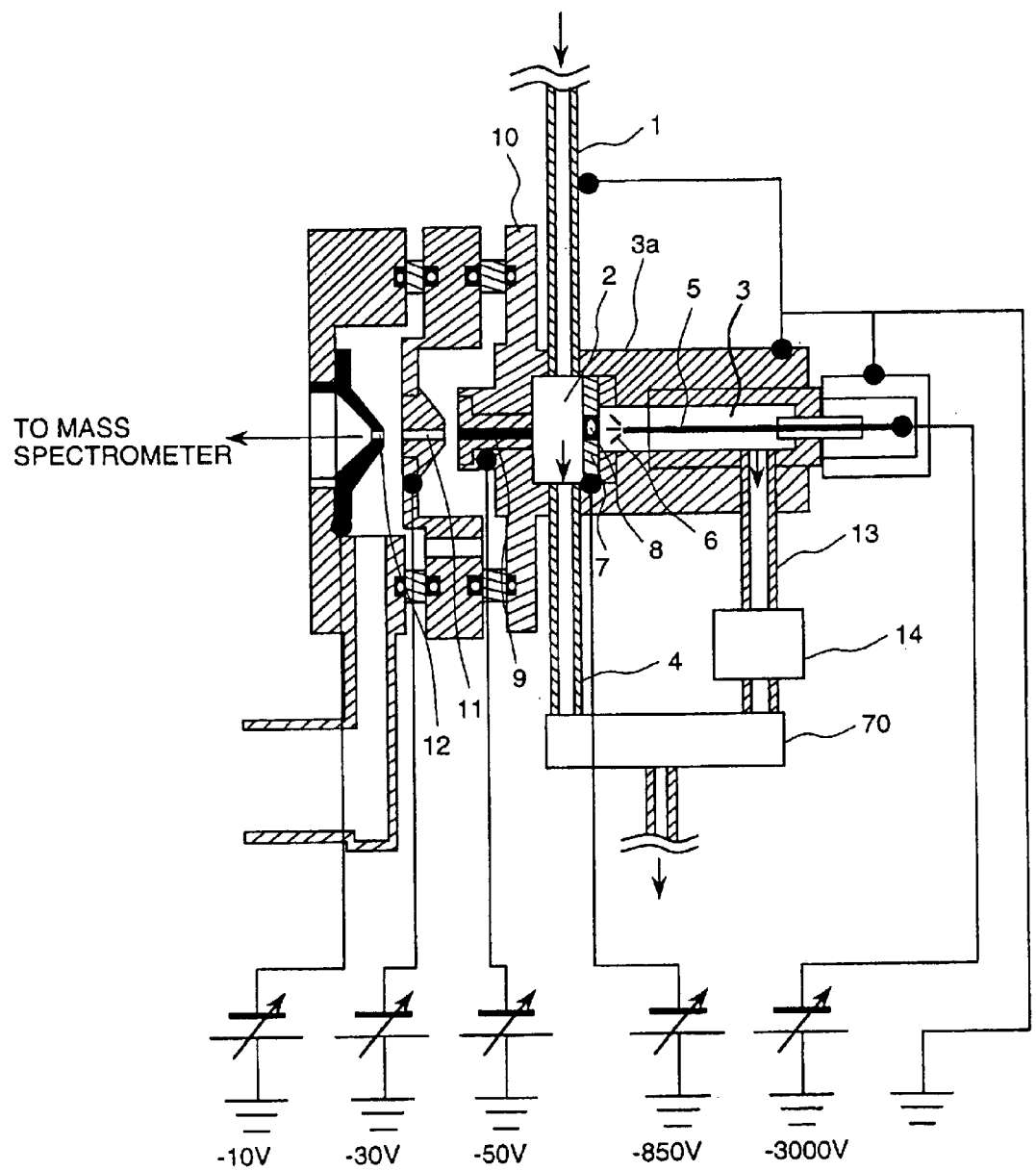
FIG. 7 is a cross-sectional diagram showing an example of voltage application in the ion source.

The voltage difference to be applied between the counter electrode 7 and the first ion sampling aperture 9 is variable depending upon the distance therebetween, but when the distance between the electrodes is about 1 to 10 mm, the voltage difference is about 10V to 2000V in absolute value. If the distance between the electrodes is too short, the discharge becomes unstable, and if the distance between the electrodes is too long, the possibility of collision of the ions onto the partitioning wall is increased so as to reduce the amount of ions passing through the opening portion 8, thereby to lower the sensitivity. For measurement of positive ions, the voltage of the counter electrode 7 is set to be higher than that of the first ion sampling aperture 9. In practice, the voltage of the counter electrode 7 is about 100 to 2000V and the voltage of the first ion sampling aperture 9 is about 10 to 200V. Conversely, for measurement of negative ions, as opposed to the case of positive ion measurement, the voltage to be applied to the counter electrode 7 is about −100 to −2000V and the voltage to be applied to the first ion sampling aperture 9 is about −10 to −200V. When negative ions are measured in the ion source of the present invention, an example of the voltage to be applied to each electrode is shown in FIG. 7.

At this time, the distance between the tip end of the needle electrode 5 and the counter electrode 7 is 3 mm, and the distance between the counter electrode 7 and the first ion sampling aperture 9 is 7 mm. It is important that the sample feed pipe 1, the corona discharge region 3 and so forth are grounded for purposes of prevention of electrical shock. For the needle electrode 5 for corona discharge, a constant voltage power source is used, as shown in FIG. 7; and, in addition, it is effective to use a constant current power source from the viewpoint of maintaining the discharge current constant. On the other hand, it is important to control the flow rate of the sample introduced into the corona discharge region 6 for measuring the ions stably and with a high precision. Therefore, in the corona discharge region 3, the sample outlet pipe 13 from the ion source and the flow controller 14 of ion source are provided to perform flow rate control in a range of about 10 to 2000 ml/min. For purposes of prevention of absorption of the sample in the ion drift region 2 and the corona discharge region 3, it is important to uniformly heat these regions. For this purpose, a cartridge heater or ceramic heater is used for heating in a range of about 50 to 400° C. This temperature is variable depending upon the sample to be measured.

It should be noted that the reference numeral 71 denotes an inner cylinder and reference numerals 72, 73 denote insulators.

A detailed discussion of the mass spectrometer will be given hereinafter. For analysis of the generated ions, various kinds of mass spectrometers can be used. The following discussion will be given for the case where an ion accumulation type ion trapping mass spectrometer is used. The same results can be obtained in the case where a quadrupole mass spectrometer performing mass separation using a high frequency electric field, a magnetic sector type mass spectrometer using mass diffusion in the magnetic field or another type of mass spectrometer is used.

The negative ions generated by the ion source used in the present invention pass through the first ion sampling aperture 9 (about 0.3 mm diameter, about 0.5 mm length), the second ion sampling aperture 11 (about 0.3 mm diameter, about 0.5 mm length) and the third ion sampling aperture 12 (about 0.3 mm diameter, about 0.5 mm length) provided in a flange type electrode 10 heated by a heater (not shown). These apertures are heated to about 100 to 300° C. by the heater (not shown). Between the first ion sampling aperture 9, the second ion sampling aperture 11 and the third ion sampling aperture 12, a voltage can be applied to improve the transmission coefficient. Also, due to collision of the residual molecules, cleavage of an ionized cluster generated by adiabatic expansion is caused to generate ions of the sample molecule. The differential discharge portion is normally discharged by a vacuum pump, such as a rotary pump, a scroll pump, a mechanical booster pump or so forth. It is also possible to use a turbo molecule pump for discharging this region. FIG. 1 shows a case where the scroll pump 70 (discharge capacity about 900 1/min) is used in the discharge of the differential discharge portion, and the turbo molecule pump 30 (discharge capacity about 200 to 300 1/min) is used. As a pump for discharging the back pressure side of the turbo molecule pump 30, a scroll pump 29 is used. The pressure between the second ion sampling aperture 11 and the third ion sampling aperture 12 is in a range of 0.1 to 1.0 Torr. It is also possible to form the differential discharge portion using two apertures, such as the first ion sampling aperture 9 and the third ion sampling aperture 12. In this case, in comparison with the foregoing case, since the inflow gas amount is increased, some measure, such as increasing the discharge speed of the vacuum pump or increasing the distance between the apertures, may be required. On the other hand, in this case, it is important to apply a voltage between both apertures.

After passing the third ion sampling aperture 12, the generated ions are concentrated at a focusing lens 15. As the focusing lens 15, an Einzel lens normally consisting of three electrodes, for example, is used. The ions then pass through an electrode 16 with a slit. By action of the focusing lens 15, the ions passing through the third ion sampling aperture 12 are focused on the slit portion. Any non-focused neutral particle or the like will collide with the electrode and be prevented from passing through this slit portion toward the mass spectrometer side. Ions which have passed through the slit in the electrode 16 will be deflected and focused by the double cylindrical type lens 19, having an inner electrode 17, provided with a large number of opening portions, and an outer electrode 18. In the double cylindrical type lens 19, deflection and focusing is performed using the electric field of the outer electrode 18 extending from the opening portion of the inner electrode. The details of this operation have been disclosed in Japanese Patent Application Laid-Open No. Heisei 7-85834 (corresponding to U.S. Pat. No. 5,481,107 to Ose et al). The disclosure of Japanese Patent Application Laid-Open No. 7-85834 (1995) is incorporated herein by reference.

Figure 5:
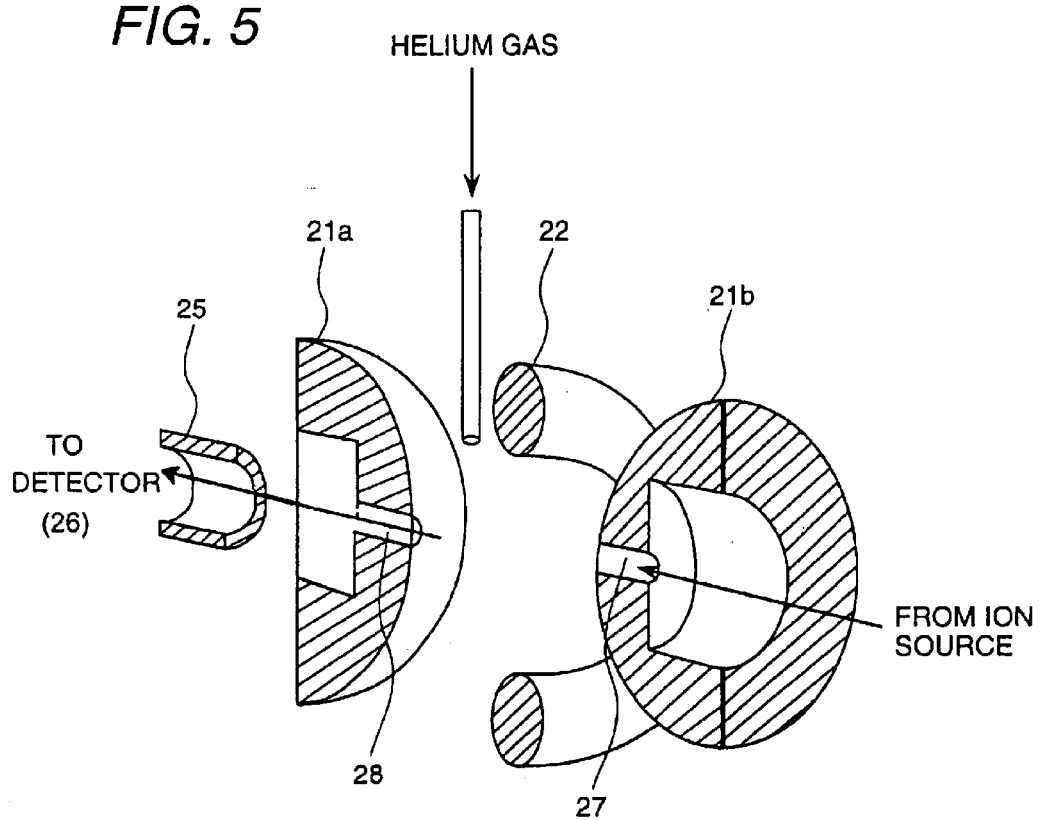
FIG. 5 is a cross-sectional diagram showing a perspective view of an ion trap portion of a mass spectrometer.

The ions which pass through the double cylindrical type lens 19 are introduced into the ion trapping mass spectrometer. An enlarged view of the ion trapping mass spectrometer of FIG. 1, which is constructed with a gate electrode 20, end cap electrodes 21a and 21b, a ring electrode 22, shielding electrodes 23a and 23b, spacer rings 24a and 24b, and an ion extraction lens 25, is shown in FIG. 5. The gate electrode 20, as shown in FIG. 1, serves to prevent introduction of the ions into the mass spectrometer from the outside, upon extracting the ions captured in the ion trapping mass spectrometer out of the ion trapping mass spectrometer. As shown in FIG. 5, the ions introduced into the ion trapping mass spectrometer through an ion sampling aperture 27 collide with a buffer gas, such helium or the like, also introduced into the ion trapping mass spectrometer, to make the raceway track smaller. Then, by scanning the high frequency voltage applied between the end cap electrodes 21a and 21b and the ring electrode 22, ions are discharged out of the ion trapping mass spectrometer from the ion sampling aperture 28 per mass number and are detected by an ion detector 26 via the ion extraction lens 25, as shown in FIG. 1. The signal produced by the detected ions is amplified by an amplifier 42, and then the signal is transferred to a data processor 43. The pressure in the ion trapping mass spectrometer, upon introduction of the buffer gas, is about $10^{-3}$ to $10^{-4}$ Torr. The mass spectrometer 100 is controlled by a mass spectrometer control portion. One of the merits of the ion trapping mass spectrometer is that it has a property of capturing ions during an accumulation period if the concentration of the sample is lean. Accordingly, even when the sample concentration is low, a high ratio condensation of the ions in the ion trapping mass spectrometer becomes possible to permit simplification of a pre-process, such as condensation of the sample or the like, to a significant extent.

Figure 6A:
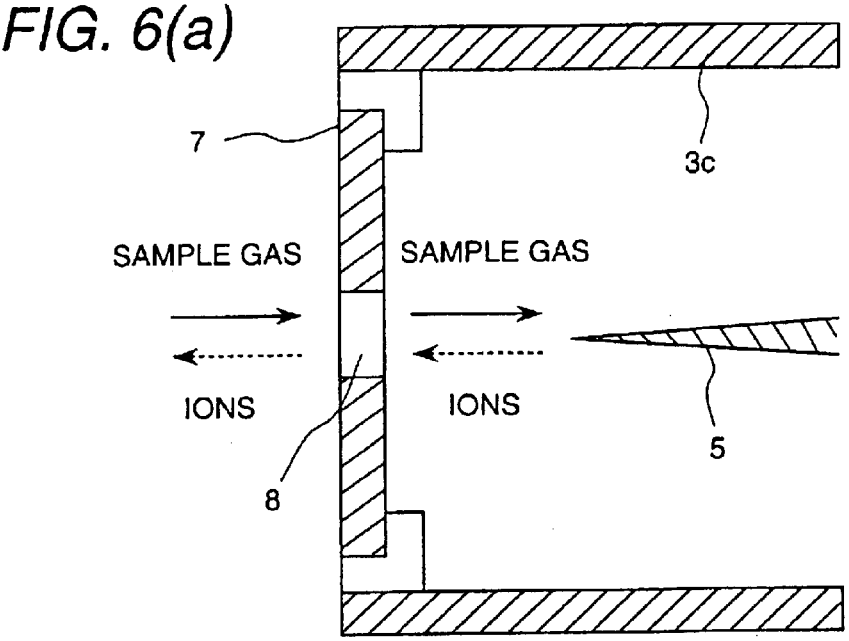
FIG. 6(a) is a cross-sectional diagram showing an opposing relationship between an ion and a sample.
Figure 6B:
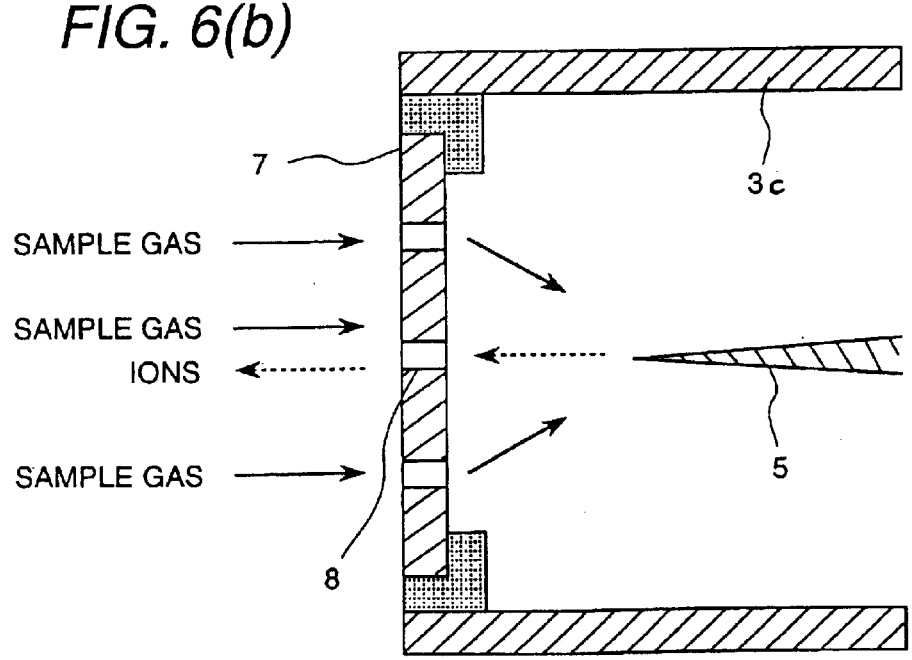
FIG. 6(b) is a cross-sectional diagram showing an opposing relationship between an ion and a sample.
Figure 6C:
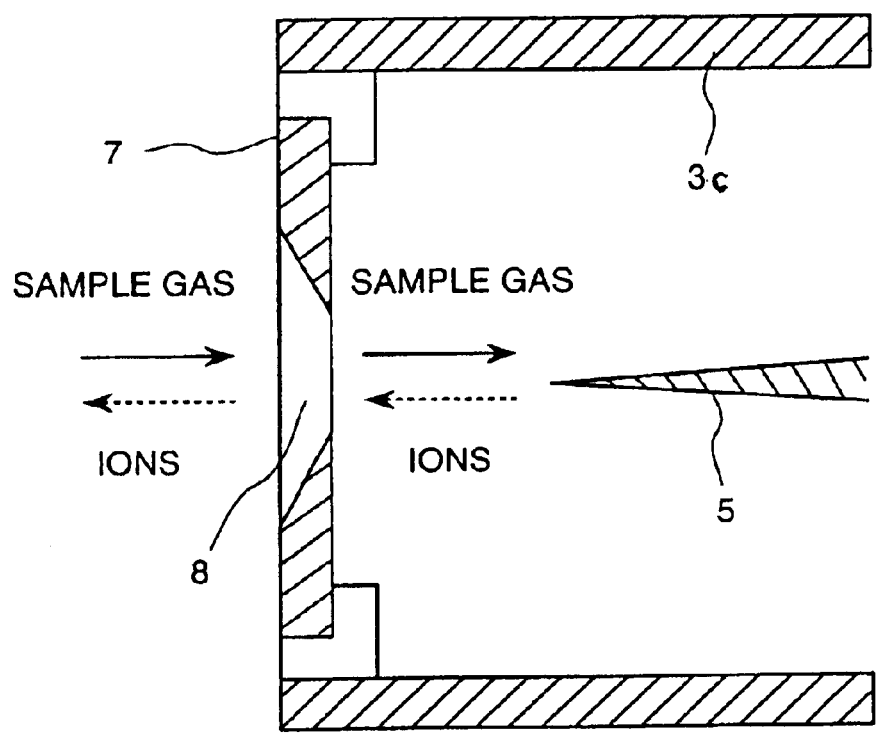
FIG. 6(c) is a cross-sectional diagram showing an opposing relationship between an ion and a sample.

FIGS. 6(a), 6(b) and 6(c) show several counter electrodes 7 of different shapes. The ions and the sampling are introduced into the corona discharge region in the manner shown in FIGS. 6(a), 6(b) and 6(c). FIG. 6(a) shows an ordinary disc-shaped counter electrode, in which the ions and the sample pass out of and into the corona charge portion, respectively, through the opening portion 8. FIG. 6(b) shows a counter electrode having a plurality of openings portions 8, in which the ions pass through the opening in the center portion and the sample passes through the openings in the circumferential portion. FIG. 6(c) shows the case where the peripheral wall which forms the opening 8 is tapered, by which ions passing through the opening 8 can be easily accelerated.

Figure 18:
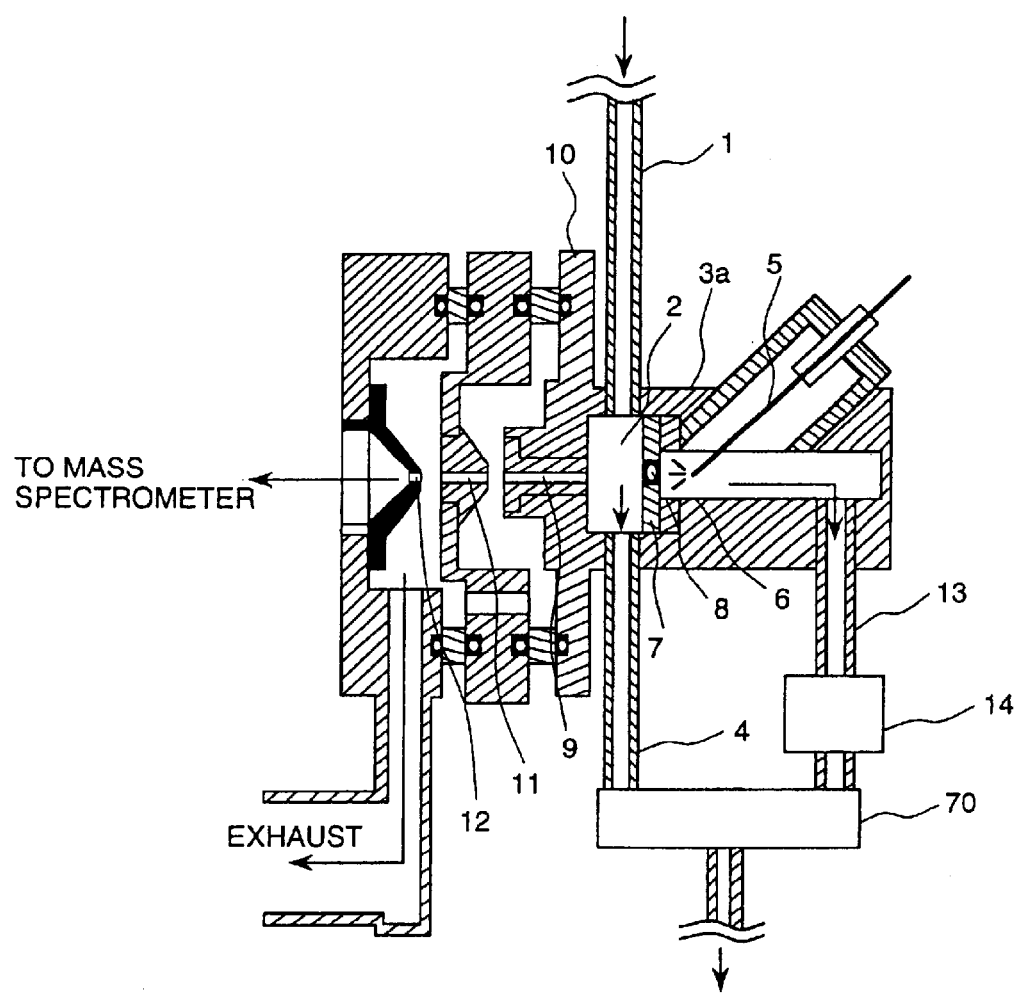
FIG. 18 is a cross-sectional view of an alternative embodiment of the ion source of FIG. 3.

FIG. 18 shows a construction, in which the direction of flow of the sample gas from the region of corona discharge and the direction of extracting the ions are different, similar to FIG. 3. However, when the orientation of the needle is to be modified, the construction shown in FIG. 18 may be employed. Even in this case, by producing a corona discharge between the tip end of the needle and the counter electrode 7, a similar effect as that achieved by the construction shown in FIG. 3 can be achieved.

Figure 19:
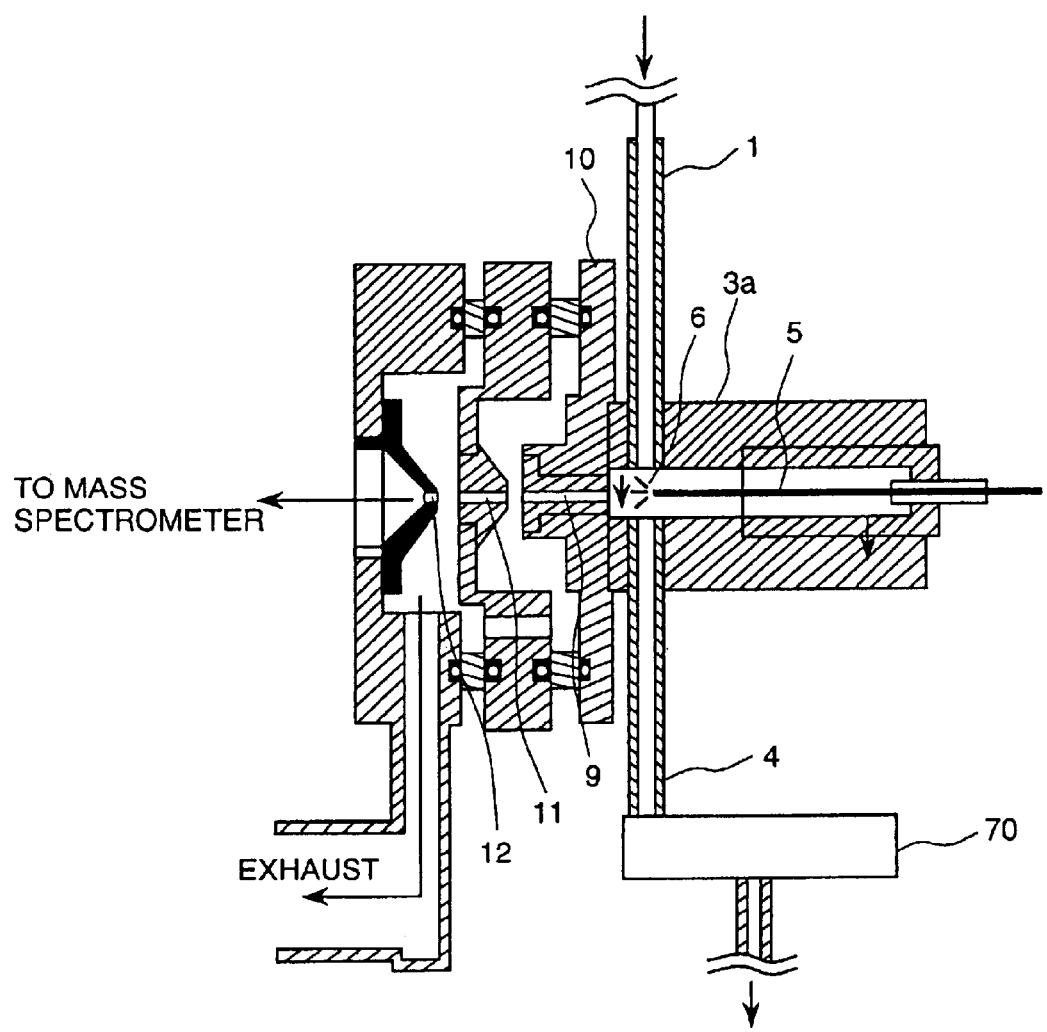
FIG. 19 is a cross-sectional view of an alternative embodiment of the ion source of FIG. 3.

FIG. 19 shows an example where the direction of flow of the sample from the corona discharge region 6 and the direction of extraction of the ions are different, but the flows are not in opposite directions. In case of FIG. 19, the direction of flow of the sample is transverse to the direction of the line connecting the tip end of the needle and the opening 9. In this case, the ions and neutral molecules move in mutually perpendicular directions. However, by increasing the flow velocity of the sample gas, a similar effect to that achieved by the construction shown in FIG. 3 can be achieved. A similar effect also can be obtained by providing a gradient differentiating moving direction, rather than an opposite or perpendicular direction.

Figure 20:
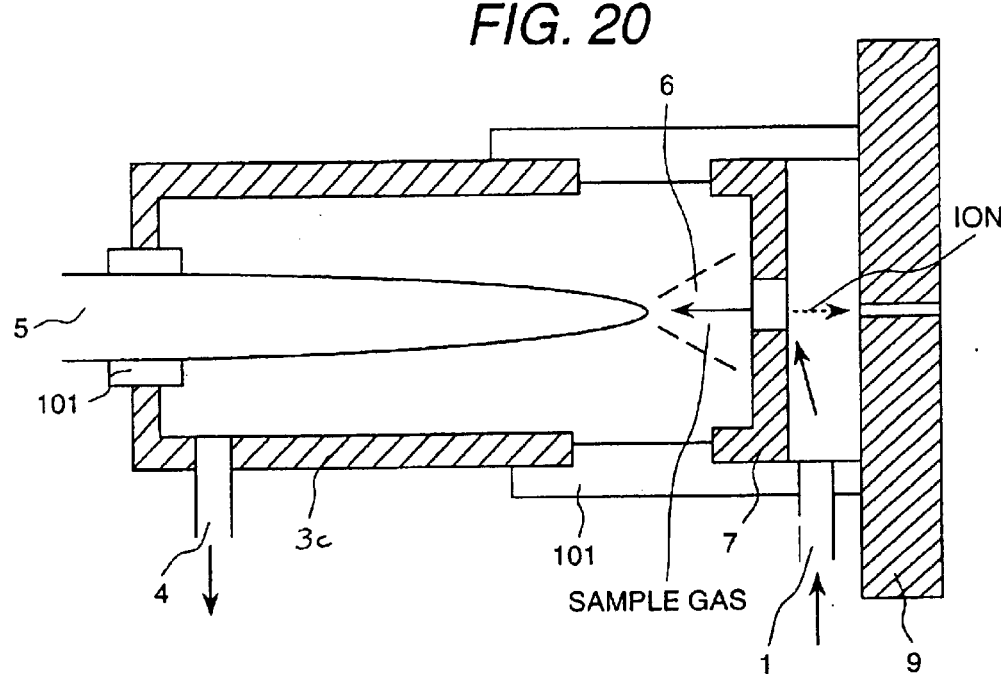
FIG. 20 is a cross-sectional diagram of an extended ion source portion.

FIG. 20 shows a construction in which the ion source of FIG. 3 is extended. By forming a gas flow at the tip end of the needle, a stable corona discharge can be maintained for a long period of time. In this case, when taking the ion generation efficiency into account, the gas is caused to flow in the direction opposite to the moving direction of the ions. As shown in FIG. 19, even when the direction of gas flow at the tip end of the needle is not opposite to the moving direction of the ions, the negative ions generated at the tip end of the needle can be sufficiently dispersed to maintain a stable corona discharge for a long period by increasing the flow velocity of the gas.

Figure 21:
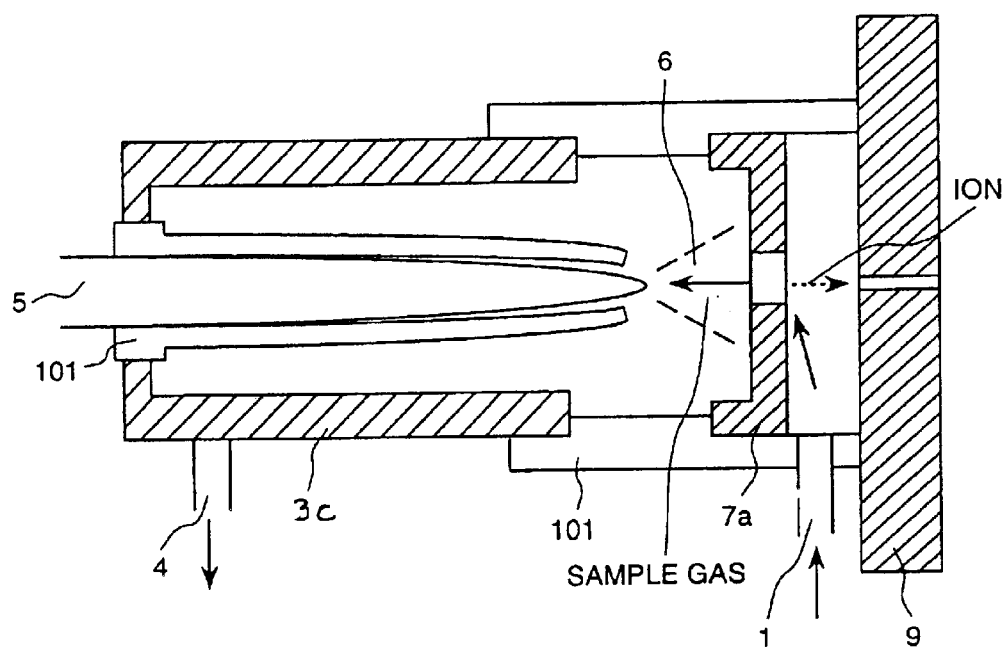
FIG. 21 is a cross-sectional diagram of an alternative embodiment of the extended ion source of FIG. 20.
Figure 22:
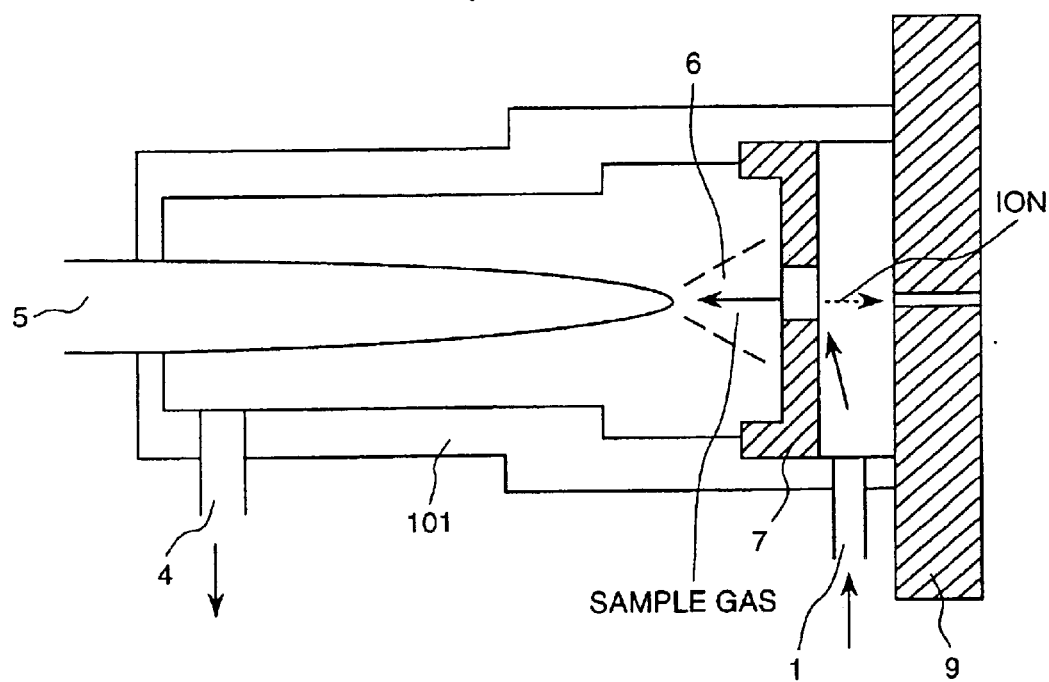
FIG. 22 is a cross-sectional diagram of an alternative embodiment of the extended ion source of FIG. 20.

FIG. 21 shows an embodiment in which the needle electrode 5, having a high voltage applied thereto, is covered with an insulator. When the ion source casing 3c is formed of a metal material to facilitate machining, it is possible to cause a discharge between the body of the needle electrode and the ion source casing. If a discharge between the needle electrode and the counter electrode 7 fails, the amount of ions which pass through the aperture of the counter electrode is significantly reduced, thereby to lower the sensitivity of the mass spectrometer. In order to prevent this, the needle electrode is covered by an insulator so as to inhibit a discharge on the peripheral surface of the body of the needle electrode, as shown in FIG. 21, or the ion source casing is formed with insulator, as shown in FIG. 22. In the alternative, it is also effective to provide sufficient distance between the ion source casing 3 and the needle electrode 5. As a rough standard, it is formed that, when the distance between the needle electrode 5 and the counter electrode 7 is about 3 mm, the distance between the side surface of the needle electrode and the ion source casing should preferably be more than or equal to 5 mm.

Figure 23:
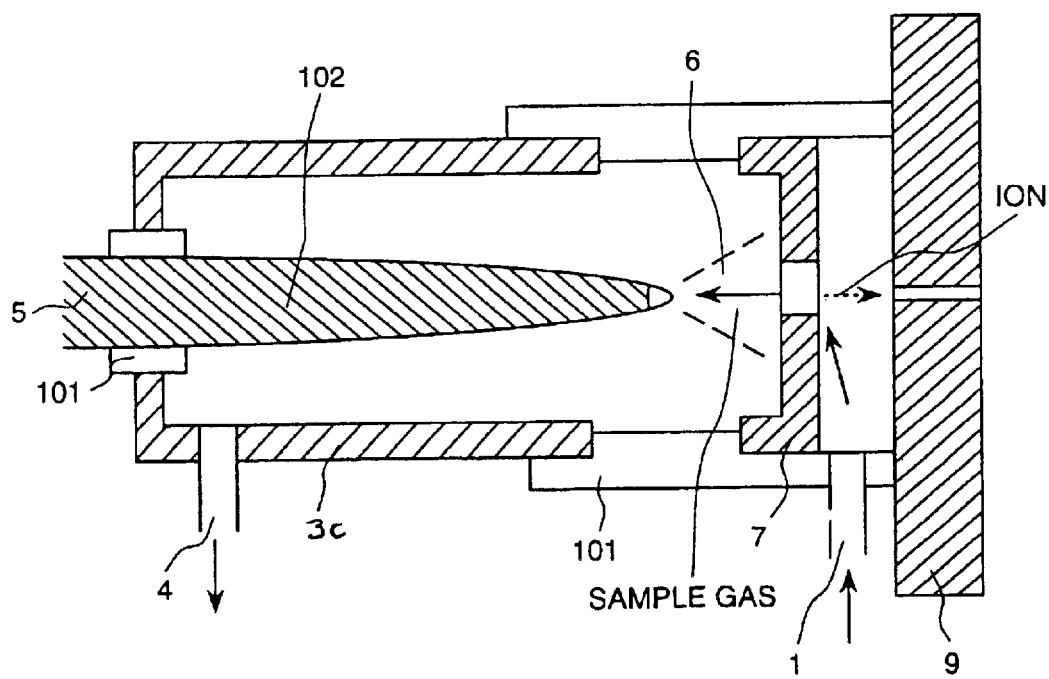
FIG. 23 is a cross-sectional diagram of an alternative embodiment of the extended ion source of FIG. 20.

On the other hand, as shown in FIG. 23, when the side surface of the needle electrode is coated with a gold plating or hard chrome plating except for the tip end of the needle, a discharge is hardly caused on the body of the needle electrode, and a normal discharge between the needle electrode and the counter electrode can be easily produced so as to maintain a stable discharge for a long period of time. Further, when a corrosive gas, such as hydrogen chloride, is used, the needle electrode formed as set forth above is effective from the view point of corrosion resistance.

Figure 8:
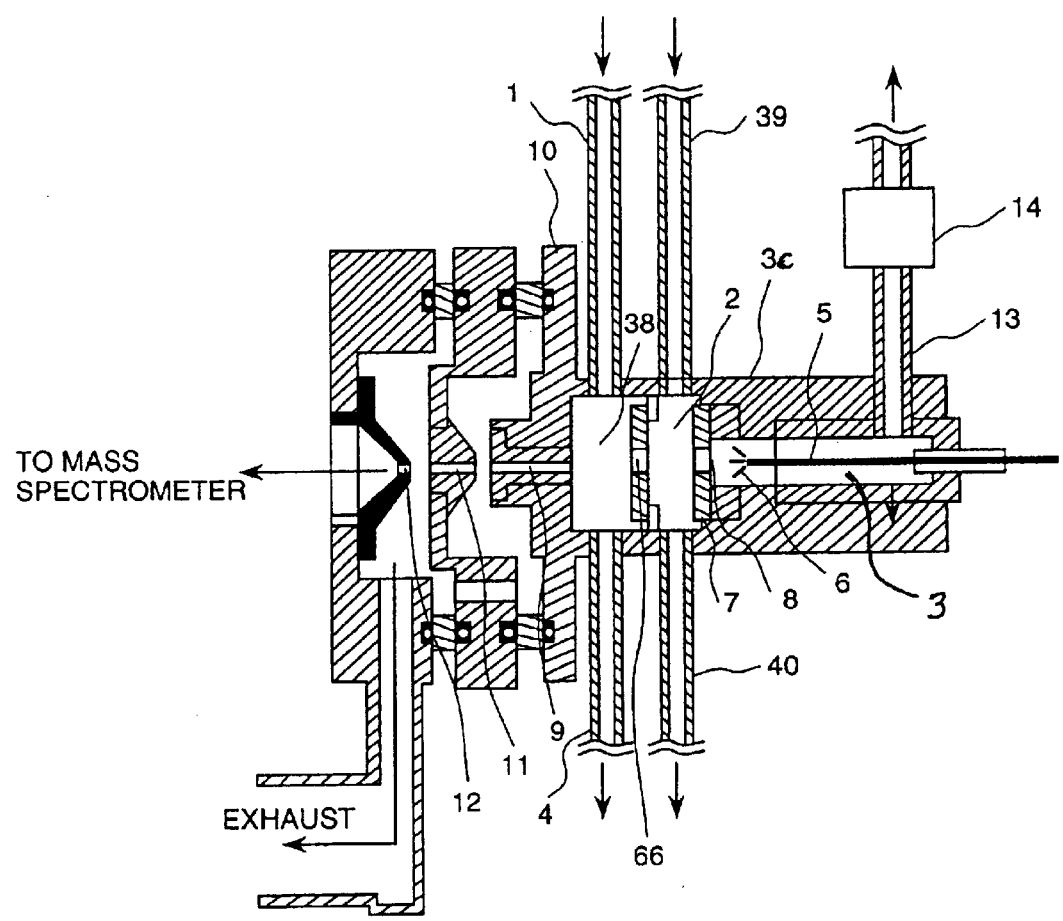
FIG. 8 is a cross-sectional diagram showing a construction of an alternative embodiment of FIG. 3.

FIG. 8 shows an alternative to the embodiment of FIG. 3, which embodiment is basically similar to FIG. 3. In the following, like components will be identified by like reference numerals and a discussion of common components will be omitted in order to avoid redundant disclosure and for keeping the disclosure simple enough to facilitate a clear understanding of the present invention.

FIG. 3 shows the case where one ion drift region is provided. However, it is also possible to provide a plurality of ion drift regions. FIG. 8 shows an embodiment where a second ion drift region 38 is provided in addition to the first ion drift region 2, at a position adjacent to the latter. One example of the operation of this embodiment is as follow. The sample gas is introduced through the sample feed pipe I and is discharged from the sample outlet pipe 4. At this time, a reactant gas, such as air, is introduced through a reactant gas inlet pipe 39. When a part of the reactant gas is introduced into the corona discharge region, on the basis of the principle discussed in the foregoing embodiment (1), mainly $O_2^-$ passes through the counter electrode 7 from the ion drift region 2. To the sample gas introduced through the sample feed pipe 1, for example, air containing chlorophenol or the like, $O_2^-$ is driven through the second counter electrode 66, ions of chlorophenol are generated. Electric fields are provided between the counter electrode 7 and the second counter electrode 66, and between the second counter electrode 66 and the first ion sampling aperture 9. The inter-electrode distance between the counter electrode 7 and the second counter electrode 66, and the distance between the second counter electrode 66 and the first ion sampling aperture 9 are both about 1 to 10 mm. In the measurement of negative ions, when about −10V is applied to the first ion sampling aperture 9, about −1 kV, −2 kV are applied to the counter electrode 7 and the second counter electrode 66, respectively. These voltages control the retention period of $O_2^-$ in the ion drift region 2, namely the reaction time. In the case where the reaction of $O_2^-$ in the ion drift region 2 is a problem, the retention period may be shortened by setting the voltage higher. The ions are introduced into the mass spectrometer through the first ion sampling aperture 9. A significant advantage of the construction set forth above is that when the sample gas is the exhaust gas of an incinerator, the exhaust gas is not introduced into the corona discharge region directly. Thereby, contamination of the needle electrode can be prevented, so as to extend its use for a long period.

Figure 9:
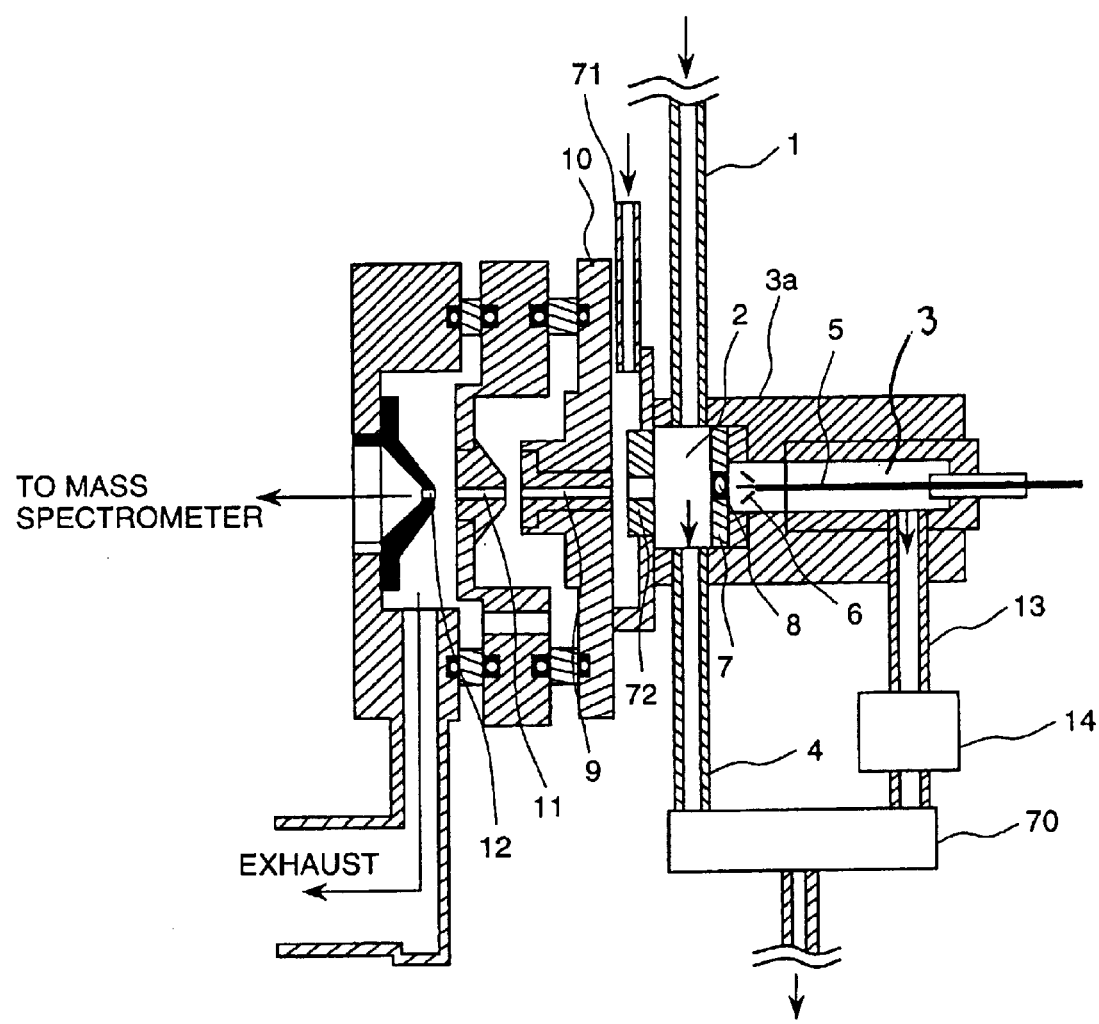
FIG. 9 is a cross-sectional showing a construction of an alternative embodiment of FIG. 3.

FIG. 9 is an alternative to the embodiment of FIG. 3 and is basically the same as that of FIG. 3. In the following, like components will be identified by like reference numerals and the discussion of common components will be omitted in order to avoid redundant disclosure and for keeping the disclosure simple enough to facilitate a clear understanding of the present invention.

In the case of FIG. 3, ions drift between the counter electrode 7 and the first ion sampling aperture 9. In contrast to this, in the present embodiment, in addition to the construction set forth above, a counter gas outlet electrode 72 is provided in front of the first ion sampling aperture 9. The distance between the first ion sampling aperture 9 and the counter gas outlet electrode 72 is 0.1 to 5 mm. At the center of the counter gas outlet electrode 72, an opening of about 2 mm diameter is formed to permit the air introduced through a counter flow gas inlet 71 to flow toward the counter electrode 7. In comparison with the diameter (about 0.25 mm) of the first ion sampling aperture 9, the opening of the counter gas outlet electrode 72 is greater. At this time, between the counter gas outlet electrode 72 and the first ion sampling aperture 9, the ions are caused to drift toward the first ion sampling aperture 9 by the electric field. When the distance between the first ion sampling aperture 9 and the counter gas outlet electrode 72 is 0.5 mm, the voltage difference between the electrodes is about 10 to 500V. With taking such construction, a particle containing liquid a droplet or dust will hardly enter into the first ion sampling aperture 9, thereby to efficiently introduce only ions into the mass spectrometer.

Figure 10:
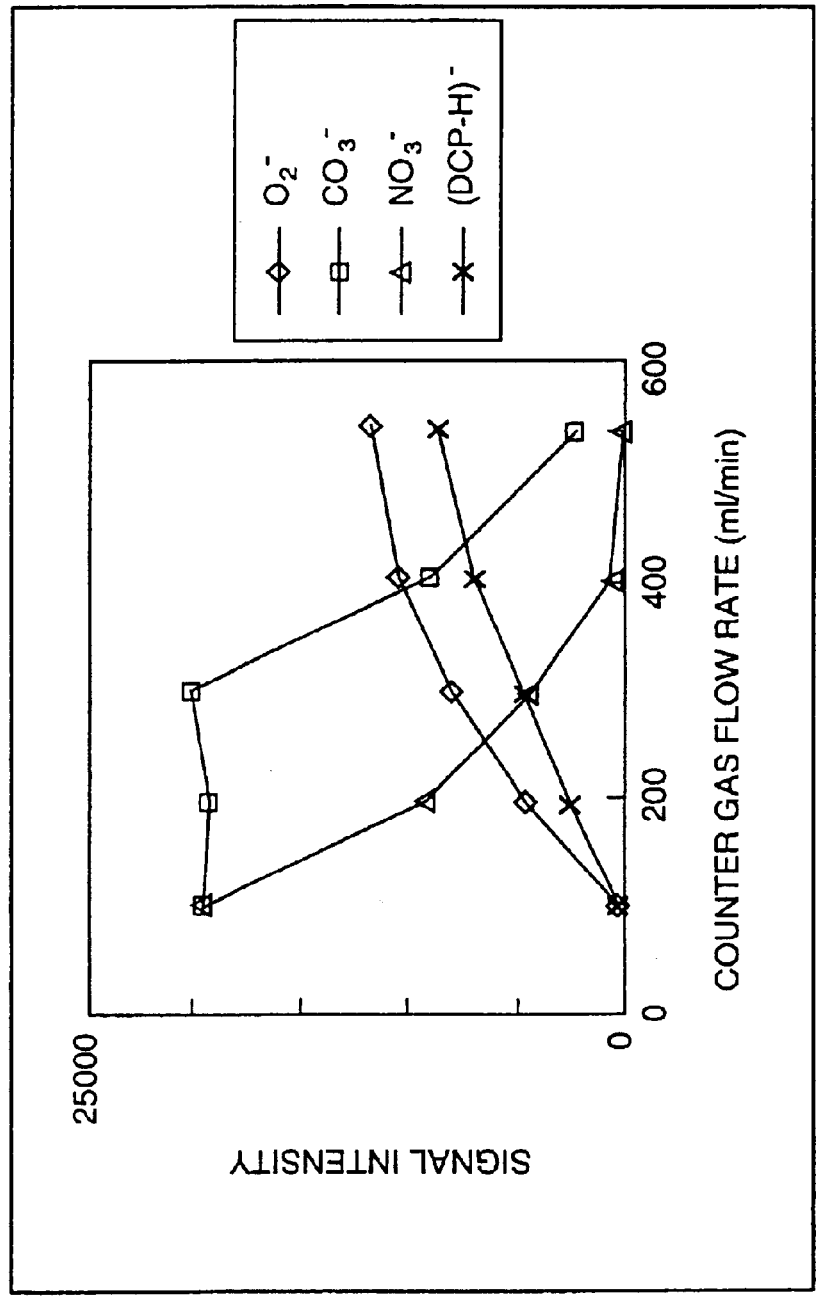
FIG. 10 is a characteristic chart.

One of important parameters of the ion source to be used in accordance with the present invention is the flow rate of the sample to be introduced into the corona discharge region 3 from the sample feed pipe 1. By setting and controlling the flow rate so that it is greater than or equal to a certain value, the ions of the sample can be stably measured with a high sensitivity. The relationship between the flow rate of the sample to be introduced into the corona discharge region 3 from the sample feed pipe 1 and ion strength of dichlorophenol or the like is shown in FIG. 10. At this time, the negative corona discharge current is 5 $\mu$A, the distance between the counter electrode and the ion sampling aperture is 7 mm and the voltage therebetween is 800V. As can be appreciated from the drawing, by setting the flow rate of the sample to be introduced into the corona discharge region from the sample feed pipe so that it is greater than or equal to about 100 ml/min, the ion strength of the dichlorophenol (corresponding to $(DCP-H)^-$) in the drawing) can be significantly increased. On the other hand, the strengths of $NO_3^-$ (ion corresponding to mass number 62), $CO_3^-$ or $N_2O_2^-$ (ion corresponding to mass number 60) are reduced according to an increase of the flow rate. In the ion source according to the present invention, the usefulness of setting the flow rate of the sample to be introduced into the corona discharge region so as to be greater than or equal to a certain value (for example, 100 ml/min) can be appreciated.

According to the increase of the flow rate of the sample to be introduced into the corona discharge region, the linear velocity of an intermediate (NO) product generated in the corona discharge region is also increased. Accordingly, the fact that period during which the intermediate product is present in the corona discharge region is shortened, can be appreciated. As a result, generation of $NO_3^-$ can be restricted to significantly increase the ion strength of the dichlorophenol (corresponding to $(DCP-H)^-$ in the drawing). The advantage of increasing of the flow rate of the sample to be introduced into the corona discharge region is as set forth above.

The $CO_3^-$ signal intensity is lowered when the sample flow rate becomes greater than or equal to 300 ml/min. When the flow rate becomes greater than or equal to 400 ml/min, the signal intensity of $O_2^-$ and $(DCP-H)^-$ become greater than either of those of $NO_3^-$ and $CO_3^-$, thereby to achieve a higher precision measurement. As set forth above, by controlling the counter gas flow, the signal intensity can be controlled.

Figure 11A:
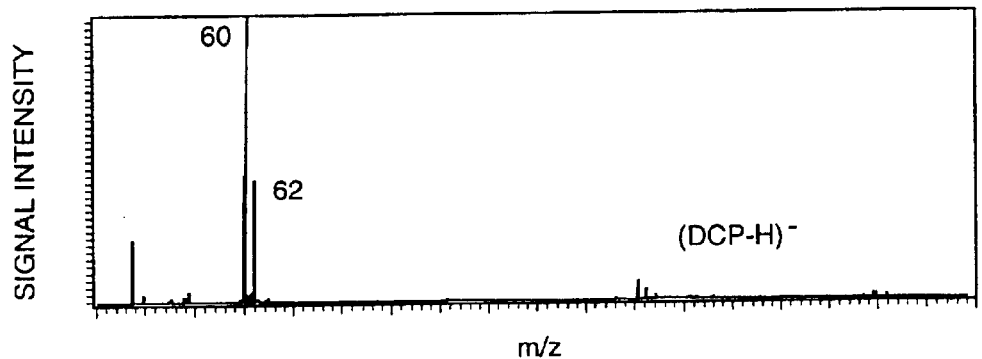
FIG. 11(a) is a view showing an example of a mass spectrum obtained by the ion source of the present invention.
Figure 11B:
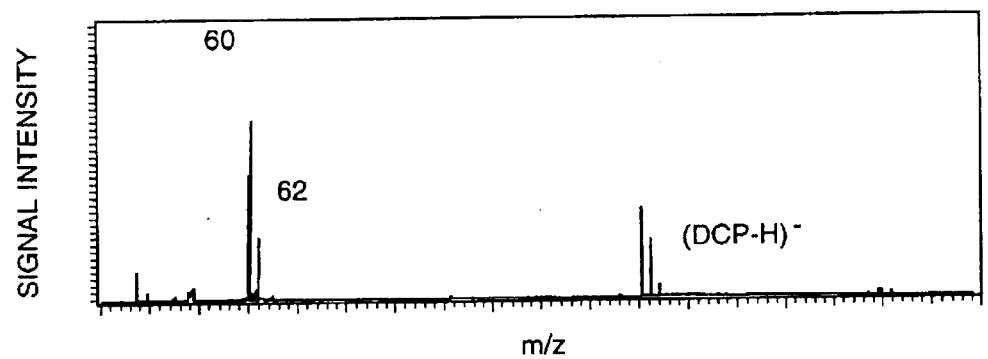
FIG. 11(b) is a view showing an example of a mass spectrum obtained by the ion source of the present invention.
Figure 11C:
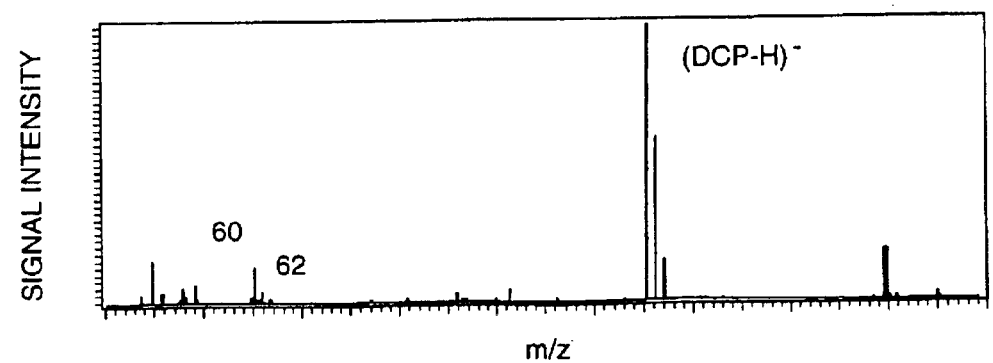
FIG. 11(c) is a view showing an example of a mass spectrum obtained by the ion source of the present invention.

By employing the ion source of the present invention, a fine component in the air can be detected with a high sensitivity. FIGS. 11(a), 11(b) and 11(c) show the difference between mass spectra obtained when a conventional ion source is used and when the present invention is used using dichlorophenol (concentration 5 $\mu$g/Nm$^3$) in the air. At this time, the negative corona discharge current is 5 $\mu$A, the distance between the counter electrode and the ion sampling aperture is 7 mm and the voltage therebetween is 800V (voltage applied to the counter electrode is –850V and voltage applied to the ion sampling aperture is –50V). In the conventional ion source, while extremely strong $NO_3^-$ is monitored, only a small amount of negative ions $(CP-H)^-$ which originate from the chlorophenol can be monitored (FIG. 11(a)). In contrast to this, in the ion source of the present invention, it can be appreciated that, in addition to the relative strength of $(CP-H)^-$ relative to $NO_3^-$, the absolute sensitivity is improved significantly (FIGS. 11(b) and 11(c)).

Here, FIGS. 11(b) and 11(c) show mass spectra obtained when the flow rates of the sample to be introduced into the corona discharge region are respectively 200 and 500 ml/min, respectively.

Application to Explosive Detector

Next, the discussion will be directed to application of the ion source according to the present invention to an explosive detector.

FIGS. 12(a), 12(b), 13(a) and 13(b) show the construction of an explosive detector 33 for detecting an explosive or a drug in a public facility, such as at an airport. For purposes of detection of an explosive, such as a nitro compound, a system using a mass spectrometer having the ion source according to the present invention is effective. In FIGS. 14(a) and 14(b), mass spectra of TNT and RDX as nitro compounds are shown, respectively. It can be appreciated that $M^-$ or $(M+NO_2)^-$ is monitored.

Figure 12A:
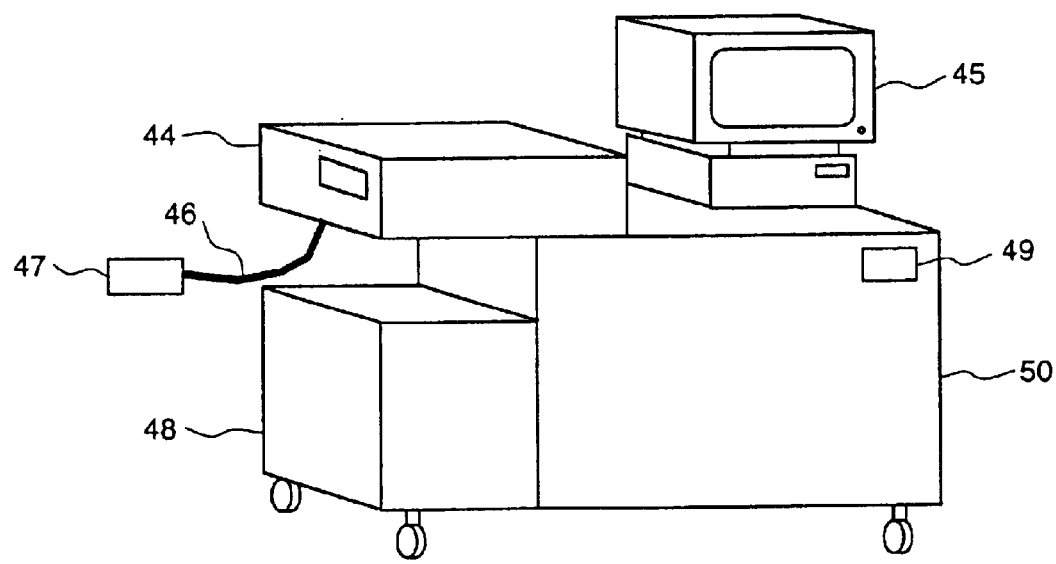
FIG. 12(a) is a perspective view showing one embodiment of explosive detection having the ion source according to the present invention.
Figure 12B:
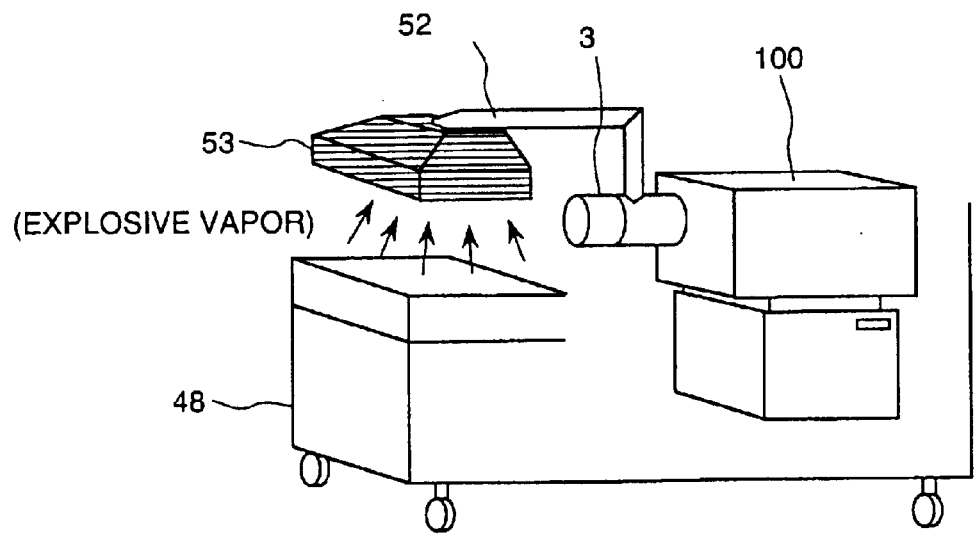
FIG. 12(b) is a perspective view showing one embodiment of explosive detection having the ion source according to the present invention.
Figure 13A:
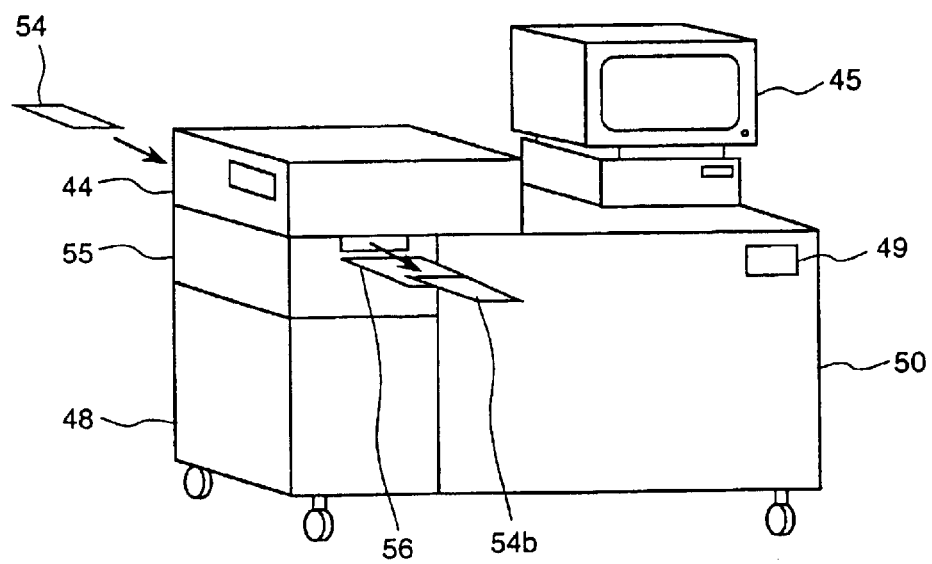
FIG. 13(a) is a perspective view showing one embodiment of explosive detection having the ion source according to the present invention.
Figure 13B:
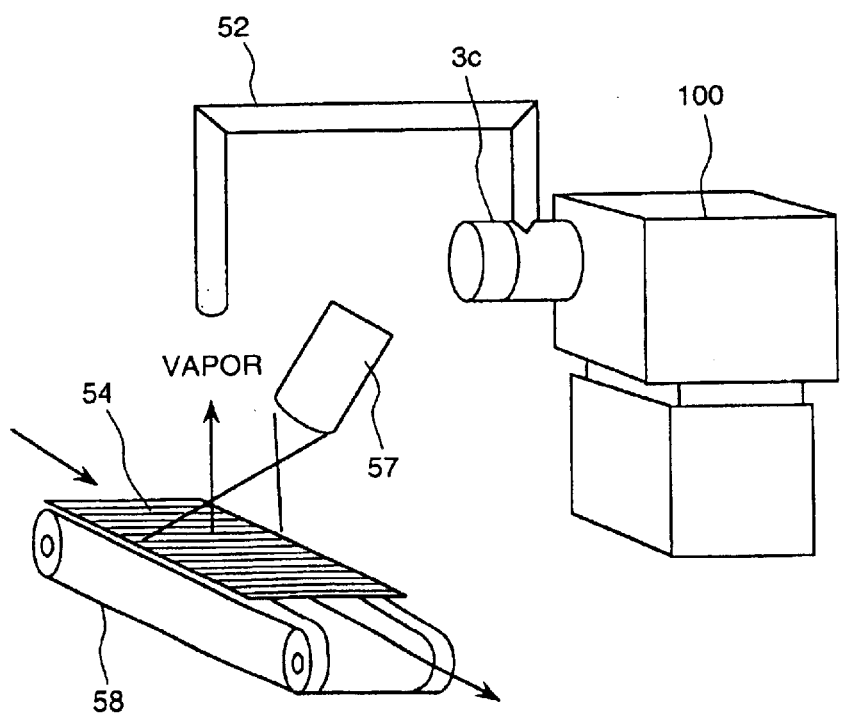
FIG. 13(b) is a perspective view showing one embodiment of explosive detection having the ion source according to the present invention.

For detection of an explosive, the presence of an explosive is checked by using a probe or a duct sucking in a sample gas, for sucking, ionizing and detecting the vapor of the explosive leaking from luggage 35 or cargo in off-line or on-line. FIG. 12(a) shows the case where a suction probe for sucking sample gas into a sample gas inlet 44, through an inlet pipe 46 from an inlet opening 47. On the other hand, FIG. 12(b) shows the case where a duct 53 is connected to a sample gas feed pipe 52 coupled to a corona discharge region 3. On the other hand, it is also possible to examine a boarding pass or passport as an object for inspection 54, as shown in FIG. 13(a). At this time, as seen in FIG. 13(b), the object for inspection 54 is moved to a position below a sample gas feed pipe 52 by a conveyer 58 located in the inspection scanner 55, and vapor of an explosive is sucked from the inspection object 54. The ions generated through the sample gas feed pipe 52 into the corona discharge region 3 are detected by the mass spectrometer 100. At this time, it is effective to heat the inspection object to a temperature higher than the room temperature (about 40 to 60° C.) using a heater 57. The inspection object 54 is held on a support 56 after inspection.

Figure 15:
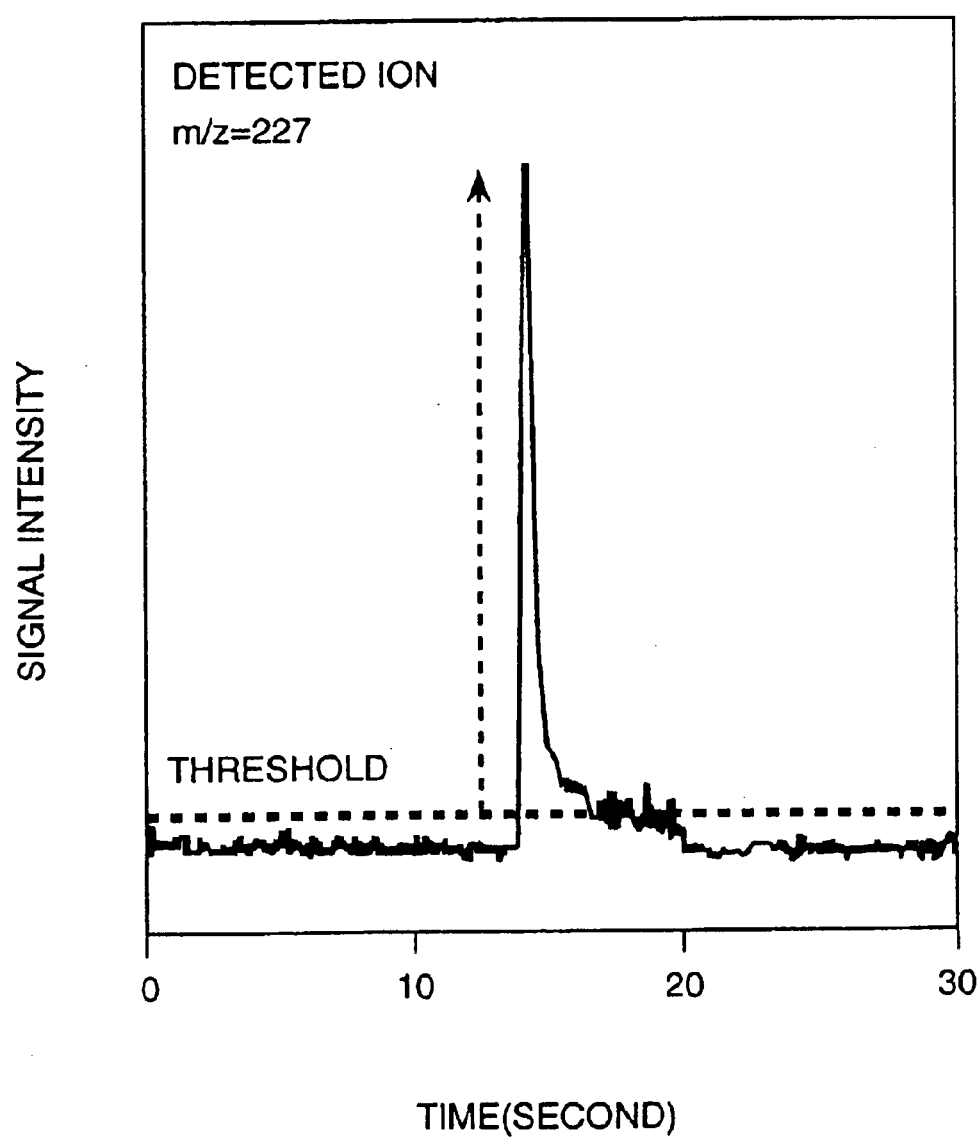
FIG. 15 is a diagram showing a display using a detection algorithm in the detection of an explosive substance.

The explosive, as typified by a nitro compound, easily generates negative ions in response to a negative corona discharge similar to an organic chlorine-based chemical compound. Therefore, the system is effective for detecting an explosive. Normally, on a display device 45 in the explosive detector 33, a variation in time of the generated ion intensity (mass chromatograph) and so forth are displayed. When an explosive, such as TNT, is present in the vapor being analyzed, the ion intensity corresponding to the molecular amount of TNT is increased. When an abnormality is not detected by this explosive detector, the luggage or other object being inspected may pass through. If an abnormality is detected, a detailed re-inspection is performed. By providing a certain threshold value in the ion intensity corresponding to the molecular amount of TNT, if the ion strength is increased beyond the threshold value, a judgment is made that TNT is present in the vapor. At this time, an algorithm is employed to regard as a signal indicating the presence of TNT only a signal produced when the sample is monitored for a predetermined period of time or longer, in order to discriminate from a mere spike of noise. By adding such an algorithm, any malfunction can be reduced. The condition is illustrated in FIG. 15. At this time, as a final display, the following case can be considered. An indicator of the substance corresponding to the ions to be detected is displayed on the display, and according to the algorithm set forth above, if A is detected, A is caused to blink to indicate detection of A. At this time, it may be possible to additionally provide an indicator indicating the extent of concentration (which may be information simply indicative of the fact that the amount is large or small) or an alarm. This is a common idea for other dangerous substances. Namely, in the case of a plastic bomb, if the explosive is present in the luggage as a thick mass, it can be detected by an X-ray inspection device. However, if the plastic bomb is in a thin sheet form, most of X-rays will pass through it so that it may be possibly overlooked by the X-ray inspection device, and thus it is difficult to detect. At this time, by using the explosive detector, the explosive can be detected as the vapor of the explosive leaks within the luggage or out of the luggage. Thus, the probability of detection of the explosive can be significantly increased in comparison with an X-ray inspection device. Also, in the case of re-inspection, whether the substance in the luggage is an explosive or not can be instantly checked by analysis of the vapor, and the kind of explosive can also be detected. Therefore, in such a case, an explosive detector having the ion source according to the present invention is more advantageous than an X-ray inspection device.

On the other hand, a similar idea is applicable for detection of medical substances, such as a drug or the like. In this case, utilizing the property of the material, such as a drug, stimulant drug or the like containing nitrogen, to have a high affinity with a proton, the positive ion originated from the drug is detected utilizing a positive corona discharge. The primary form of the ions generated from a drug or the like is the form where a proton is added to the molecule of $(M+H)^+$.

It is important to provide casters 50 for the explosive detector to make it movable. It is also important to provide a simple monitor control portion 49 to facilitate start up of the device.

Application to Liquid Chromatography

Figure 16:
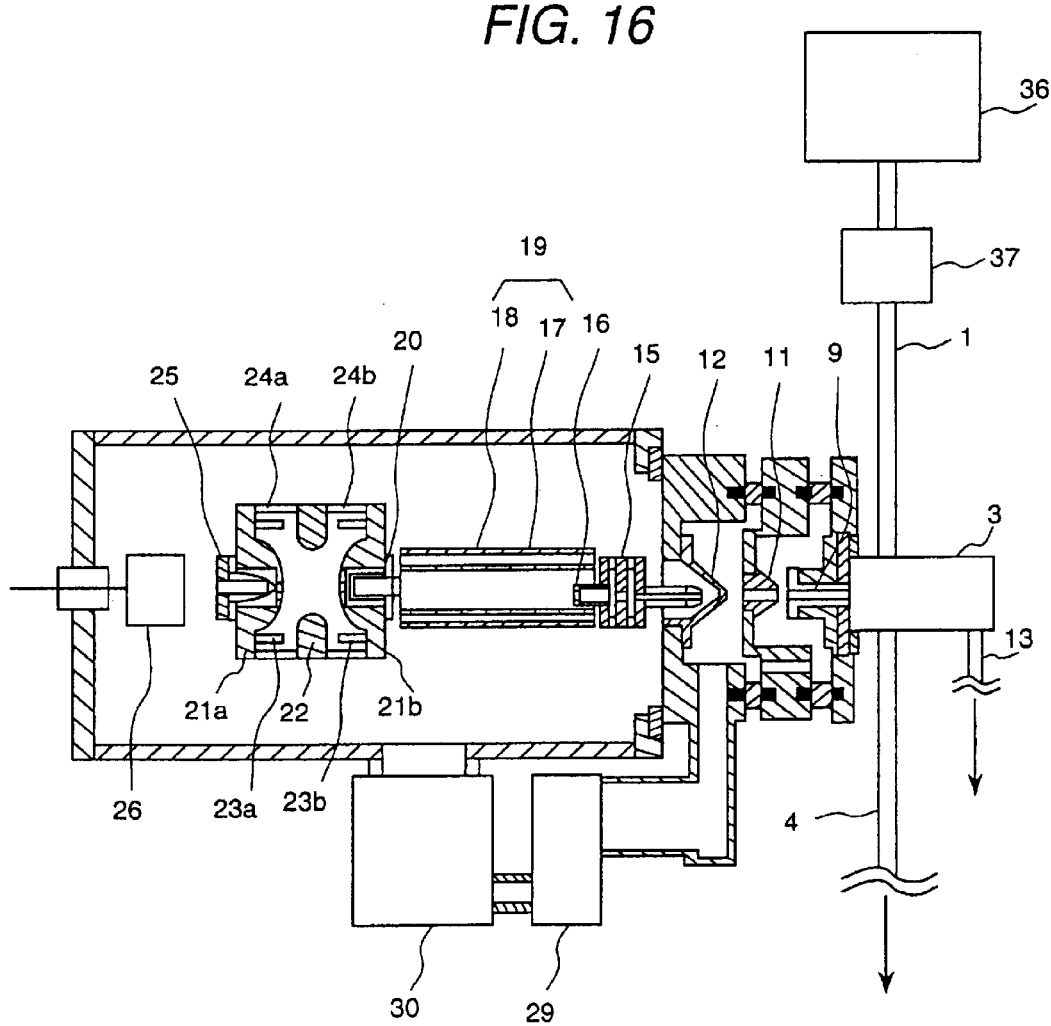
FIG. 16 is a cross-sectional view showing one example of a mass spectrometer with the ion source according to the present invention.
Figure 17:
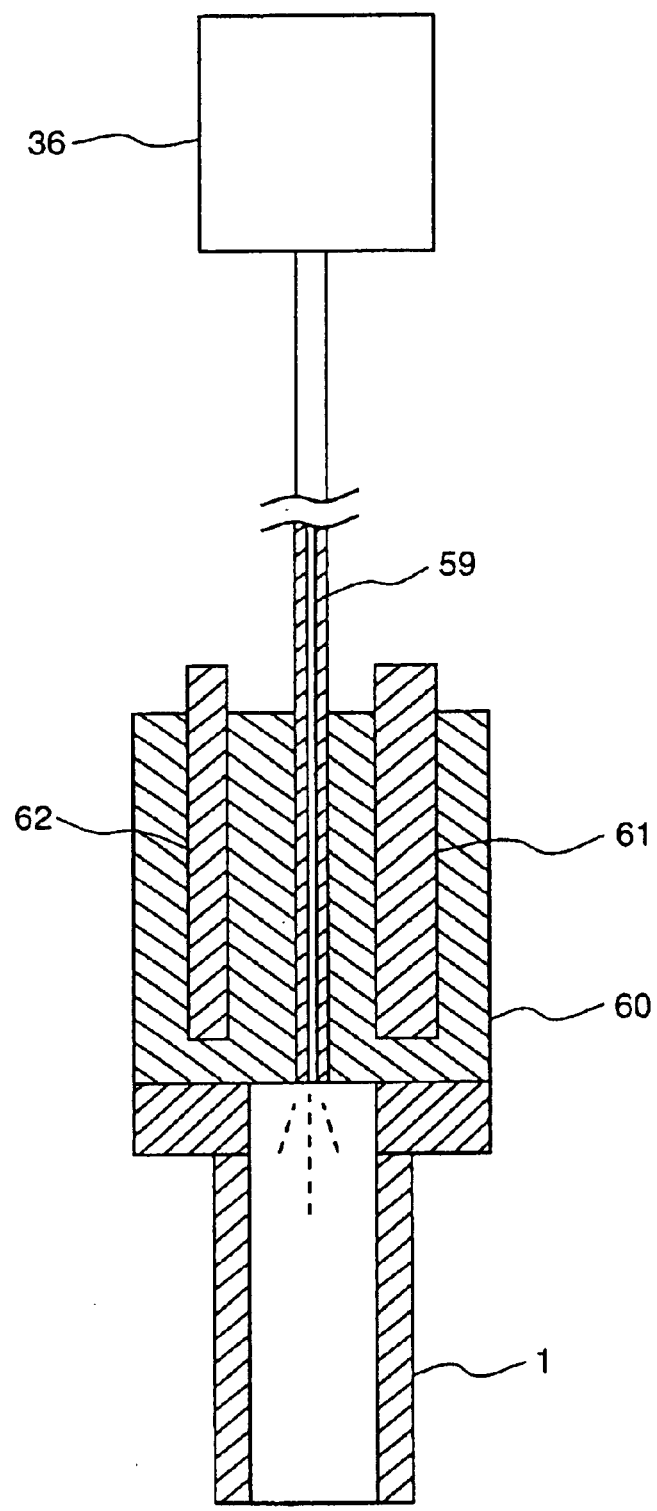
FIG. 17 is a cross-sectional diagram of an example of a vaporizer to be employed in the liquid chromatographic mass spectrometer.

The ion source according to the present invention is further applicable as the ion source to be used in a liquid chromatograph mass spectrometer. An example of the construction of a liquid chromatograph mass spectrometer is shown in FIG. 16. Namely, an eluate from the liquid chromatograph 36 is vaporized by an appropriate vaporizer (comprising a conduit 59 for spraying by heating or by gas). Then, the vapor is introduced into the ion source of the present invention to be subjected to ionization, and the generated ions are detected by the mass spectrometer. Employing the ion source of the present invention, since the sample can be ionized with a high efficiency, the sensitivity in detection can significantly enhanced. In FIG. 17, a heating type vaporizer 37 is employed. Namely, a metal block 60 is welded to the conduit 59. The temperature of the metal block 60 can be controlled by a thermocouple 62 and a cartridge heater 61. The eluate from the liquid chromatograph 36 is converted into fine liquid droplets at the terminal end of the conduit 59.

As set forth above, according to the present invention, since the direction of flow of the sample into the corona discharge region and the direction of ion extraction from the corona discharge are different. Therefore, the period during which intermediate in the corona discharge region can be shortened. Therefore, the ions of an objective sample can be efficiently generated. Also, according to the present invention, high selectivity and high sensitivity measurement of the ions of the sample become possible. In addition, even when substances are deposited at the tip end of the needle electrode, the discharge can be maintained stably for a long period, for example two months or more.

Although the present invention has been illustrated and described with respect to exemplary embodiments thereof, it should be understood by those skilled in the art that the foregoing and various other changes, omissions and additions may be made therein and thereto, without departing from the spirit and scope of the present invention. Therefore, the present invention should not be understood as limited, to the specific embodiments set out above, but is meant to include all possible embodiments which can be embodied within the scope encompassed and equivalents thereof with respect to the feature set out in the appended claims.

What is claimed is:

1. A measuring system comprising:

a mass spectrometer comprising a chamber which includes an opening for introducing a sample gas into the chamber, and a needle electrode for ionizing said sample gas by corona discharge at a tip end of the needle electrode caused by application of a voltage to the needle electrode; and means for restricting a signal strength with respect to a mass number of $NO_3^-$ generated by a negative corona discharge in a region of said corona discharge by restricting $NO_3^-$ generating reaction by reaction of $O_2^-$ and NO for measuring a fine component in said sample gas selected among a group of chlorophenols, dioxins, chlorobenzens, hydrocarbons, nitro compounds as a precursor of said dioxins.

2. A measuring system comprising:

a mass spectrometer comprising a chamber which includes an opening for introducing a sample gas into the chamber, and a needle electrode for ionizing said sample gas by corona discharge at a tip end of the needle electrode caused by application of a voltage to the needle electrode; and means for measuring a signal strength of dichlorophenol with respect to a mass number of $NO_3^-$ generated as intermediate by $O_2^-$ by restricting the signal strength to be smaller than that of dichlorophenol.

3. An explosive detector comprising:

a probe for sampling a sample gas;

a first chamber for introducing said sample gas from said probe;

a needle electrode arranged within said first chamber;

a first opening portion for introducing ions generated in said first chamber into a mass spectrometric portion;

a second opening portion for supplying said sample gas, said second opening portion being located so that an angle formed by a direction connecting said first opening portion and a tip end of said needle electrode, and a direction connecting a center of said second opening portion and said tip end of said needle electrode is less than or equal to 90°; and a display for displaying a result of judgment made by a mass spectrometric portion.

4. An explosive detector comprising:

an inspection object scanning portion for inspecting an object;

a suction device for sucking a sample gas from said inspection object scanning portion;

a first chamber for introducing said sample gas from said suction device;

a needle electrode arranged within said first chamber;

a first opening portion for introducing ions generated in said first chamber into a mass spectrometric portion;

a second opening portion for supplying said sample gas, said second opening portion being located so that an angle formed by a direction connecting said first opening portion and a tip end of said needle electrode, and a direction connecting a center of said second opening and said tip end of said needle electrode is less than or equal to 90°; and a mass spectrometric portion for making judgment.

5. An explosive detector as claimed in claim 4, wherein said inspection object scanning portion samples said inspection object using said sample gas, while said inspection object is moving on a movable base.

* * * * *